(12) United States Patent
Burnette et al.

(10) Patent No.: US 11,109,756 B2
(45) Date of Patent: Sep. 7, 2021

(54) INTELLIGENT WIRELESS COMMUNICATIONS FOR CONTINUOUS ANALYTE MONITORING

(71) Applicant: DexCom, Inc., San Diego, CA (US)

(72) Inventors: Douglas William Burnette, San Diego, CA (US); Eric Cohen, San Diego, CA (US); Jason Halac, Solana Beach, CA (US); Hari Hampapuram, Carlsbad, CA (US); Lauren Hruby Jepson, San Diego, CA (US); Shawn Larvenz, Ramona, CA (US); Aditya Mandapaka, San Diego, CA (US); Michael Robert Mensinger, San Diego, CA (US); Jorge Valdes, San Diego, CA (US); Jeffrey R. Wedekind, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 1195 days.

(21) Appl. No.: 15/384,944

(22) Filed: Dec. 20, 2016

(65) Prior Publication Data
US 2017/0181628 A1     Jun. 29, 2017

Related U.S. Application Data

(60) Provisional application No. 62/271,880, filed on Dec. 28, 2015.

(51) Int. Cl.
*A61B 5/145* (2006.01)
*A61B 5/00* (2006.01)
(Continued)

(52) U.S. Cl.
CPC .......... *A61B 5/0004* (2013.01); *A61B 5/0024* (2013.01); *A61B 5/1495* (2013.01);
(Continued)

(58) Field of Classification Search
CPC ...... A61B 5/14532; A61B 5/746; H04Q 9/00; H04Q 2209/823; H04Q 2213/13095; H04Q 2209/86; H04Q 2209/40; H04Q 2209/82
See application file for complete search history.

(56) References Cited

U.S. PATENT DOCUMENTS 6,001,067 A    12/1999  Shults et al.
6,424,847 B1    6/2002  Mastrototaro et al.
(Continued)

FOREIGN PATENT DOCUMENTS

WO    WO 2015/069797    5/2015
WO    WO 2015/094981    6/2015

OTHER PUBLICATIONS

European Extended Search Report dated May 5, 2019 for Application No. 16882378.9.
(Continued)

*Primary Examiner* — Meredith Weare
(74) *Attorney, Agent, or Firm* — Knobbe Martens Olson & Bear LLP

(57) ABSTRACT

Various embodiments relate generally to continuous monitoring of analyte values received from an analyte sensor system. In some example embodiments, there is provided a method that includes receiving sensor information, calculating and storing estimated analyte measurement values based upon the received sensor information. The method also includes determining one or more communication conditions, and instructing a transceiver to advertise to a first (Continued)

display device in accordance with one or more communication variables based upon the one or more communication conditions. The method then transmits the estimated analyte measurement values to the at least first display device. Related systems, methods, and articles of manufacture are also described.

28 Claims, 17 Drawing Sheets

(51) Int. Cl.
    *G16H 40/63*     (2018.01)
    *H04L 29/08*     (2006.01)
    *G16H 40/67*     (2018.01)
    *A61B 5/1495*     (2006.01)
    *H04Q 9/00*     (2006.01)

(52) U.S. Cl.
CPC ........ *A61B 5/14532* (2013.01); *A61B 5/7275* (2013.01); *A61B 5/7282* (2013.01); *A61B 5/742* (2013.01); *A61B 5/746* (2013.01); *A61B 5/7445* (2013.01); *G16H 40/63* (2018.01); *G16H 40/67* (2018.01); *H04L 67/12* (2013.01); *H04Q 9/00* (2013.01); *H04Q 2209/40* (2013.01); *H04Q 2209/82* (2013.01); *H04Q 2209/823* (2013.01); *H04Q 2209/86* (2013.01); *H04Q 2213/13095* (2013.01)

(56) References Cited

U.S. PATENT DOCUMENTS

| | | | |
|---|---|---|---|
| 6,477,395 B2 | 11/2002 | Schulman et al. | |
| 6,484,046 B1 | 11/2002 | Say et al. | |
| 6,512,939 B1 | 1/2003 | Colvin et al. | |
| 6,565,509 B1 | 5/2003 | Say et al. | |
| 6,579,690 B1 | 6/2003 | Bonnecaze et al. | |
| 6,931,327 B2 | 8/2005 | Goode et al. | |
| 7,310,544 B2 | 12/2007 | Brister et al. | |
| 2005/0027463 A1 | 2/2005 | Goode et al. | |
| 2005/0043598 A1 | 2/2005 | Goode et al. | |
| 2005/0154271 A1 | 7/2005 | Rasdal et al. | |
| 2005/0192557 A1 | 9/2005 | Brauker et al. | |
| 2005/0203360 A1 | 9/2005 | Brauker et al. | |
| 2006/0004270 A1 | 1/2006 | Bedard et al. | |
| 2006/0020187 A1 | 1/2006 | Brister et al. | |
| 2006/0222566 A1 | 10/2006 | Brauker et al. | |
| 2007/0016381 A1 | 1/2007 | Kamath et al. | |
| 2007/0027385 A1 | 2/2007 | Brister et al. | |
| 2007/0032706 A1 | 2/2007 | Kamath et al. | |
| 2007/0197890 A1 | 8/2007 | Boock et al. | |
| 2007/0203966 A1 | 8/2007 | Brauker et al. | |
| 2007/0208245 A1 | 9/2007 | Brauker et al. | |
| 2008/0033254 A1 | 2/2008 | Kamath et al. | |
| 2008/0108942 A1 | 5/2008 | Brister et al. | |
| 2008/0119703 A1 | 5/2008 | Brister et al. | |
| 2009/0240120 A1 | 9/2009 | Mensinger et al. | |
| 2010/0331645 A1* | 12/2010 | Simpson et al. ..... | A61B 5/1468 600/347 |
| 2014/0187889 A1 | 7/2014 | Cohen et al. | |
| 2014/0243749 A1* | 8/2014 | Edwards et al. ..... | H04B 1/3827 604/187 |
| 2014/0266776 A1* | 9/2014 | Miller et al. ......... | A61B 5/0002 340/870.01 |
| 2015/0038818 A1* | 2/2015 | Cole ...................... | A61B 5/746 600/365 |
| 2015/0123810 A1 | 5/2015 | Hernandez-Rosas et al. | |
| 2015/0164391 A1 | 6/2015 | Hernandez-Rosas et al. | |
| 2015/0190100 A1* | 7/2015 | Fox et al. ................ | A61B 5/00 340/539.12 |

OTHER PUBLICATIONS

International Preliminary Report on Patentability for Application No. PCT/US2016/067830 dated Jul. 12, 2018, 13 pages.
International Search Report and Written Opinion for Application No. PCT/US2016/067830 dated Mar. 17, 2017, 13 pages.

* cited by examiner

INTELLIGENT WIRELESS COMMUNICATIONS FOR CONTINUOUS ANALYTE MONITORING

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Appl. No. 62/271,880, filed on Dec. 28, 2015. The aforementioned application is incorporated by reference herein in its entirety, and is hereby expressly made a part of this specification.

FIELD

Various embodiments relate generally to continuous monitoring of analyte values received from an analyte sensor system.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic person will normally only measure his or her glucose level two to four times per day. Unfortunately, these time intervals are spread so far apart that the diabetic person will likely find out too late, sometimes incurring dangerous side effects, of a hyperglycemic or hypoglycemic condition. In fact, it is not only unlikely that a diabetic person will take a timely SMBG value, but it is also unlikely that the diabetic will know if his or her blood glucose value is going up (higher) or down (lower) utilizing conventional monitoring systems and methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale. In some aspects of the disclosed technology, a computer-implemented method includes receiving sensor information; calculating and storing estimated analyte measurement values based upon the received sensor information; determining one or more communication conditions; instructing a transceiver to advertise to at least a first display device in accordance with one or more communication variables based upon the one or more communication conditions; and transmitting the estimated analyte measurement values to the at least first display device. In some implementations, the computer-implemented method further includes determining the one or more communication conditions comprises determining at least one of the following: a time associated with the communication conditions; historical communication conditions; an existence of an alarm condition; a condition of the continuous glucose monitoring sensor; a condition of a user of the continuous glucose monitoring sensor; and whitelist conditions. In some implementations, the one or more communication variables includes at least one of an advertising duration parameter and an advertising interval parameter according to which advertising beacons are transmitted to the first display device, and wherein the at least one of the advertising duration and advertising interval parameters are adjusted to the first display device. In some implementations, the first display device includes one of a last-connected display device populating the whitelist, a preferred display device populating the whitelist, and a display device configured to advertise to at least a second display device. In some implementations, the alarm condition comprises a determination that the condition of the user is approaching or experiencing a medically critical state. In some implementations, the one or more communication variables are optimized for establishing a wireless communication session with the first display device. In some implementations, the optimization of the one or more communication variables includes at least one of increasing a default advertising duration parameter and decreasing a default advertising interval parameter. In some examples, the one or more communication variables are optimized for establishing a wireless communication session with the first display device upon a determination that the estimated analyte measurement values are indicative of a trend towards a medically critical state. In some implementations, the one or more communication variables are adjusted for delaying establishment of a wireless communication session with the first display device upon a determination that the estimated analyte measurement values are indicative of a trend towards a medically non-critical state.

In some aspects of the disclosed technology, an apparatus includes signal conditioning circuitry communicatively connected to a continuous analyte sensor for receiving sensor information from the continuous analyte sensor indicative of analyte levels of a host to which the continuous analyte sensor is operatively attached; a processor, wherein upon receiving the sensor information from the signal conditioning circuitry, instructs a radio to perform the following: transmit a plurality of advertising beacons to a first display device in accordance with one or more communication variables based upon one or more communication conditions determined by the apparatus; and upon the first display device responding to one of the plurality of advertising beacons, establish a wireless communication session with the first display device and transmit the sensor information or analyte values derived from the sensor information to the at least first display device. In some implementations, the one or more communication variables includes at least one of: a transmission frequency variable indicating a frequency with which the sensor information or the analyte values are transmitted to the first display device; a transmission protocol indicating a wireless communication protocol to be utilized in the transmission of the sensor information or the analyte values to the first display device; a communications type variable indicating a one-way communication or a two-way communication with the first display during the transmission of the sensor information or the analyte values to the first display device; and a transmission occurrence variable indicating whether the transmission of the sensor information or the analyte values to the first display device are to occur in an on-demand or automatic manner. In some implementations, the one or more communication variables further includes: a data packet format type variable to be utilized for the transmission of the plurality of advertising beacons; an advertising duration variable indicative of a duration for which the first display device is to be advertised to; an advertising interval variable indicative of an amount of time between the transmission of each of the plurality of advertising beacons; and a power variable indicative of power to be used by the radio for the transmission of the advertising beacons. In some implementations, the one or more communication variables further includes a display device type variable indicating a type of at least one of the first display device and additional display devices to which the sensor information or analyte values are to be sent; a display device number indicating a number of display devices available to receive the sensor information or analyte values; an order variable indicating a connection order of display devices previously having established a wireless communication session with the radio; a role variable indicating whether at least one of the first display device and the additional display devices are at least one of a primary display device, a secondary display device, a preferred display device, a scan-only display device, an advertising display device, and a sensor information or analyte values forwarding display device; and a broadcast mode variable indicating one-way or two-way broadcasting to be used in conjunction with at least one of the first display device and the additional display devices if the at least one of the first display device and the additional display devices comprise an advertising display device or a sensor information or analyte values forwarding display device.

In some aspects of the disclosed technology, a computer-implemented method, includes calculating and storing estimated glucose value data based upon glucose measurements obtained by a continuous glucose monitoring sensor; determining one or more communication conditions; and advertising to one or more display devices in a manner based on the one or more communication conditions. In some implementations, the determination of the one or more communication conditions includes analyzing historical estimated glucose value data. In some implementations, the analysis of the historical estimated glucose value data results in an observed trend. In some implementations, the determination of the one or more communication conditions further includes determining whether an alarm condition exists based on the observed trend. In some implementations, the advertising to the one or more displays includes incorporating the estimated glucose value data in advertising beacons upon a determination that no alarm condition exists. In some implementations, the estimated glucose value data is incorporated in the advertising beacons in an encrypted format. In some implementations, the advertising to the one or more displays includes transmitting advertising beacons to the one or more display devices upon a determination that an alarm condition exists. In some examples, the computer-implemented method further includes establishing wireless communication sessions during which the estimated glucose value data is transmitted to the one or more display devices upon the one or more display devices responding to their respective advertising beacons.

In some aspects of the disclosed technology, an apparatus includes: a continuous analyte sensor adapted to obtain raw analyte data; a processor and a memory unit having computer code configured to cause the processor to: calculate and store analyte value data derived from the raw analyte data; determine one or more communication conditions; and a radio adapted to advertise to one or more display devices in a manner based on the one or more communication conditions.

In some aspects of the disclosed technology, an apparatus includes a memory; and a processor, the memory having computer code configured to cause the processor to: receive estimated glucose value data; and based upon observed communication conditions and communication variables adapted based on the observed communication conditions, transmit the estimated glucose value data to one or more display devices.

Any of the features of aspects specified herein are applicable to all other aspects and embodiments identified herein. Moreover, any of the features of an aspect is independently combinable, partly or wholly with other aspects described herein in any way, e.g., one, two, or three or more aspects may be combinable in whole or in part. Further, any of the features of an aspect may be made optional to other aspects. Any aspect of a method can be performed by a system or apparatus of another aspect, and any aspect or of a system can be configured to perform a method of another aspect.

BRIEF DESCRIPTION OF THE DRAWINGS

Various embodiments are described in detail with reference to the accompanying figures. The drawings are provided for purposes of illustration only and merely depict typical or example embodiments. These drawings are provided to facilitate the reader's understanding of the systems and methods described herein, and shall not be considered limiting of the breadth, scope, or applicability of the various embodiments.

DETAILED DESCRIPTION

Figure 1:
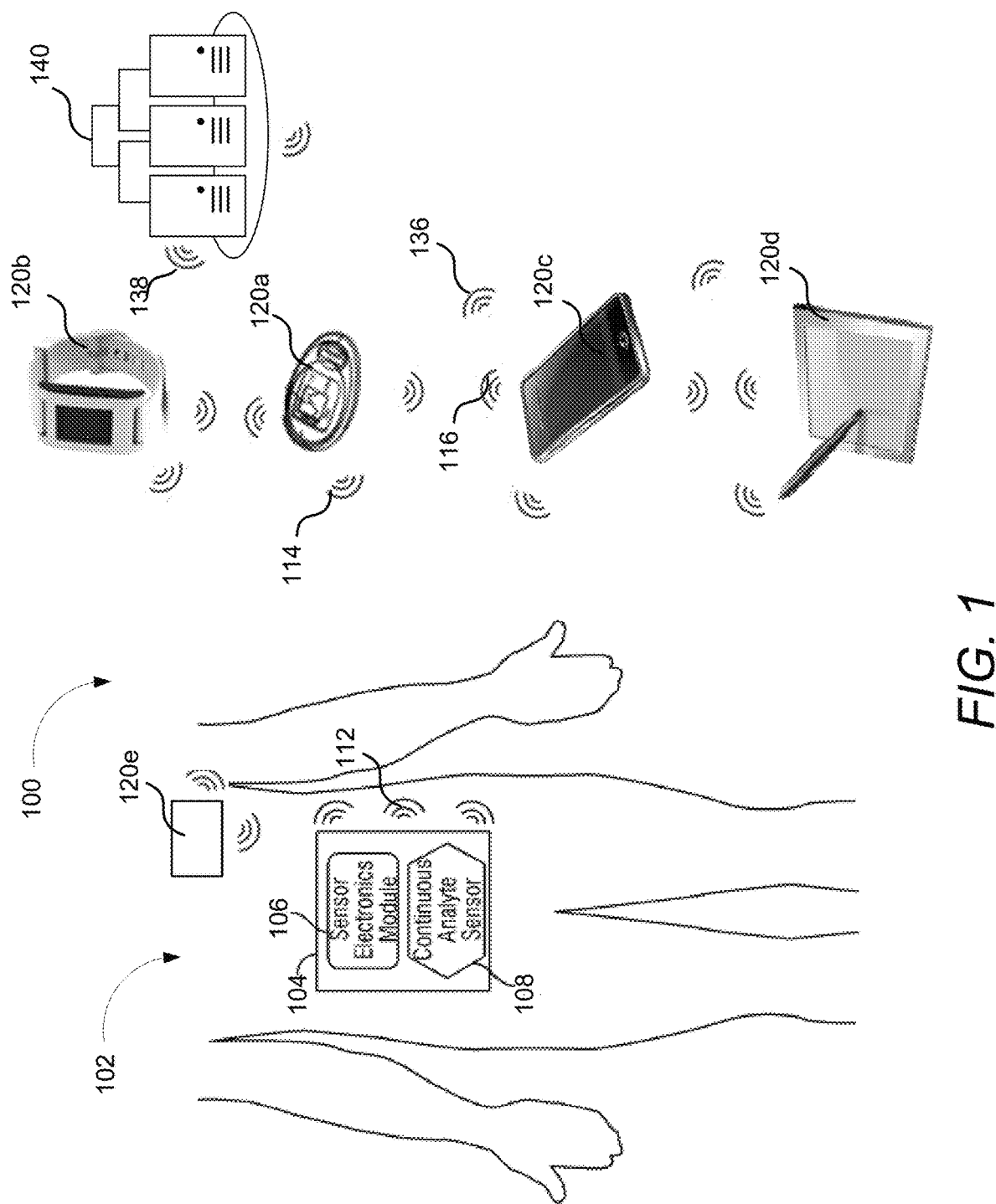
FIG. 1 is a diagram illustrating certain embodiments of an example continuous analyte sensor system communicating with at least one display device in accordance with various technologies described in the present disclosure.

The following description illustrates some example embodiments of the disclosed technology or technologies in detail. Those of skill in the art will recognize that there are numerous variations and modifications of the disclosed embodiments encompassed by its scope. Accordingly, the description of a certain example embodiments should not be deemed to limit the scope of the present disclosure.

Overview

As alluded to previously, continuous monitoring of blood glucose values, one example of an analyte (discussed in greater detail below) can improve upon conventional monitoring systems and methods by improving comfort and convenience, as well as lessening the chance that a person's deteriorating or medically critical condition goes unnoticed. Thus, various embodiments described herein are directed to systems and methods of continuous analyte monitoring and the optimization of communications/initiating communications for the transmittal and receipt of continually monitored analyte data.

In some embodiments, a system is provided for continuous measurement of an analyte in a host that can include: a continuous analyte sensor configured to continuously measure a concentration of the analyte in the host; and a sensor electronics module physically connected to the continuous analyte sensor to receive the analyte concentration measurements and communicate them to display devices. In particular, the sensor electronics module includes electronics configured to process a data stream associated with an analyte concentration measured by the continuous analyte sensor in order to generate sensor information that includes raw sensor data, transformed sensor data, and/or any other sensor data or data derived therefrom, e.g., predictive or trend data. The sensor electronics module may further be configured to generate sensor information that is customized for respective display devices, such that different display devices may receive different sensor information for presentation to the host, a host care taker, etc.

Communications between the sensor electronics module and one or more display devices can be controlled via an advertising and connection protocol indicating, for example, how often and/or how long the sensor electronics module advertises to a display device, the order in which the sensor electronics module advertised to a display device, etc. The sensor electronics module may comprise a communications unit operative in accordance with the advertising and connection protocol, such as a radio transceiver, that effectuates such communications between the sensor electronics module and the one or more display devices. The control effectuated by the advertising and connection protocol can be achieved by varying or adjusting variables or parameters that can impact communications in accordance with one or more communication conditions that can be accounted for.

As can be appreciated, the nature of continual analyte measurement, as well as a desired form factor for the sensor electronics module would be well-served by a power efficient design. Thus, the initiation of communication between the sensor electronics module and display devices, as well as communications themselves are optimized in accordance with various embodiments so as to maximize battery life in the sensor electronics module. In addition to power savings, this optimization can improve connection reliability between the sensor electronics module and display devices, as well as reduce connection delays and/or delays associated with presenting sensor information to the host.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free B-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

Display Devices

In some embodiments, the sensor electronics module may be configured to search for and/or attempt to wirelessly communicate with a display device, such as one from a list of display devices (also referred to as a whitelist). This list of display devices reflects those display devices that have successfully been paired or bonded with the sensor electronics module. For example, a display device may respond to an advertising signal transmitted by the sensor electronics module. Upon receiving this response, the list may be updated with an identifier indicative of the display device. In some embodiments, a display device may be removed from the list after some predetermined time of inactivity, e.g., no communications between the sensor electronics module and the display device. In some embodiments, another list (referred to as a bonding list) may be utilized to maintain a listing of display devices that were previously paired to or bonded with the sensor electronics module. Re-pairing a display device to the sensor electronics module can be avoided when utilizing a bonding list. For example, if a display device is removed from the whitelist, e.g., due to some predetermined amount of inactivity, the identifier of that display device may be stored in the bonding list. In other embodiments, upon pairing or bonding/inclusion in the whitelist, the display device identifier may also be stored in the bonding list. In this way, the bonding list can be accessed upon the sensor electronics module receiving a response to an advertising signal from a display device to check whether or not the display device was previously bonded to the sensor electronics module. If so, a data connection can be established without engaging in authentication (discussed below with respect to FIG. 4).

In some embodiments, the search for and/or attempted wireless communication can occur in a predetermined and/or programmable order (e.g., grading and/or escalating). For example, if an attempt at communicating with and/or alarming a first display device fails, this failure triggers an attempt to communicate with and/or alarm a second display device, and so on. It should be noted that the sensor electronics module is not necessarily tied to a single display device. Rather the sensor electronics module is configured to communicate with a plurality of different display devices directly, systematically, simultaneously (e.g., via broadcasting), regularly, periodically, randomly, on-demand, in response to a query, based on alerts or alarms, and/or the like.

The sensor information may comprise transformed sensor information that does not require processing by the display device prior to display of the sensor information. However, some display devices may comprise software including display instructions (software programming comprising instructions configured to display the sensor information and optionally query the sensor electronics module to obtain the sensor information) configured to enable display of the sensor information thereon. In some embodiments, the display device is programmed with the display instructions at the manufacturer and can include security and/or authentication to avoid plagiarism of the display device. In some embodiments, a display device is configured to display the sensor information via a downloadable program (for example, a downloadable Java Script via the internet), such that any display device that supports downloading of a program (for example, any display device that supports Java applets) can be configured to display displayable sensor information (e.g., mobile phones, tablets, PDAs, PCs and the like).

In some embodiments, certain display devices may be in direct wireless communication with the sensor electronics module, although intermediate network hardware, firmware, and/or software can be included within the direct wireless communication. In some embodiments, a repeater (e.g., a Bluetooth repeater) can be used to re-transmit the transmitted sensor information to a location farther away than the immediate range of the telemetry module of the sensor electronics module. In some embodiments, a receiver (e.g., Bluetooth receiver) can be used to re-transmit the transmitted sensor information to a display device, e.g., a TV screen, possibly in a different format, such as in a text message. In certain embodiments, the sensor electronics module transmits sensor information to one or more display devices, where the sensor information transmitted from the sensor electronics module is received by the display device without intermediate processing of the sensor information.

In some embodiments, one or more display devices are configured to query the sensor electronics module for sensor information, where the display device requests sensor information from the sensor electronics module in an "on-demand" fashion, for example, in response to a query. In some embodiments, the sensor electronics module is configured for periodic, systematic, regular, irregular or aperiodic transmission of sensor information to one or more display devices (for example, every 1, 2, 5, or 10 minutes or more). In some embodiments, the sensor electronics module is configured to transmit data packages associated with a triggered alert (e.g., triggered by one or more alert conditions). However, any combination of the above-described statuses of data transmission can be implemented with any combination of a paired sensor electronics module and display device(s). For example, one or more display devices can be configured for querying a sensor electronics module database and for receiving alarm information triggered by one or more alarm conditions being met. Additionally, the sensor electronics module can be configured to transmit sensor information to one or more display devices (the same or different display devices as described in the previous example), where the display devices function differently with regard to how they obtain sensor information.

In some embodiments, as described in more detail below, a display device is configured to query data storage memory in the sensor electronics module for certain types of data content, including direct queries into a database in the sensor electronics module's memory and/or requests for configured or configurable packages of data content therefrom; namely, the data stored in the sensor electronics module is configurable, queryable, predetermined, and/or pre-packaged, based on the display device with which the sensor electronics module is communicating. In some additional or alternative embodiments, the sensor electronics module generates the sensor information based on its knowledge of which display device is to receive a particular transmission. Additionally, some display devices are capable of obtaining calibration information and wirelessly transmitting the calibration information to the sensor electronics module, such as through manual entry of the calibration information, automatic delivery of the calibration information, and/or an integral reference analyte monitor incorporated into the display device. U.S. Patent Publication Nos. 2006/0222566, 2007/0203966, 2007/0208245, and 2005/0154271, all of which are incorporated herein by reference in their entirety, describe systems and methods for providing an integral reference analyte monitor incorporated into a display device and/or other calibration methods that can be implemented with embodiments disclosed herein.

In general, a plurality of display devices (e.g., a custom analyte monitoring device, a mobile phone, a tablet, a smart watch, a reference analyte monitor, a medicament delivery device, a medical device and a personal computer) may be configured to wirelessly communicate with the sensor electronics module. The one or more display devices can be configured to display at least some of the sensor information wirelessly communicated by the sensor electronics module. The sensor information may include, for example, sensor data, such as raw data and/or transformed sensor data, such as analyte concentration values, rate of change information, trend information, alert information, sensor diagnostic information, calibration information, non-visual information such as temperature readings, sound, etc.

Example Configurations

FIG. 1 is a diagram depicting an example continuous analyte monitoring system 100 including an analyte sensor system 104 operatively connected to a host 102 and a plurality of display devices 120 according to certain aspects of the present disclosure. For ease of reference, reference number 120 may be used to refer to the plurality of display devices together as a group, whereas respective alphanumeric reference numbers 120a, 120b, 120c, 120d, and/or 120e may be used to refer to specific display devices. It should be noted that display device 120e alternatively or in addition to being a display device, may be a medicament delivery device that can act cooperatively with the analyte sensor system 104 to deliver medicaments to host 102. The analyte sensor system 104 may include a sensor electronics module 106 and a continuous analyte sensor 108 associated with the sensor electronics module 106. The sensor electronics module 106 may be in direct wireless communication with one or more of the plurality of the display devices 120 via wireless communications signals. As will be discussed in greater detail below, display devices 120 may also communicate amongst each other and/or through each other to analyte sensor system 104. For ease of reference, wireless communications signals from analyte sensor system 104 to display devices 120 can be referred to as "uplink" signals 112. Wireless communications signals from, e.g., display devices 120 to analyte sensor system 104 can be referred to as "downlink" signals 114. Wireless communication signals between two or more of display devices 120 may be referred to as "crosslink" signals 116. Additionally, wireless communication signals may include data transmitted by one or more of display devices 120a-d via "long-range" uplink signals 136 (e.g., cellular signals) to one or more remote servers 140 or network entities, such as cloud-based servers or databases, and receive long-range downlink signals 138 transmitted by remote servers 140.

The sensor electronics module 106 includes sensor electronics that are configured to process sensor information and generate transformed sensor information. In certain embodiments, the sensor electronics module 106 includes electronic circuitry associated with measuring and processing data from continuous analyte sensor 108, including prospective algorithms associated with processing and calibration of the continuous analyte sensor data. The sensor electronics module 106 can be integral with (non-releasably attached to) or releasably attachable to the continuous analyte sensor 108 achieving a physical connection therebetween. The sensor electronics module 106 may include hardware, firmware, and/or software that enables analyte level measurement. For example, the sensor electronics module 106 can include a potentiostat, a power source for providing power to continuous analyte sensor 108, other components useful for signal processing and data storage, and a telemetry module for transmitting data from itself to one or more display devices 120. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety for all purposes.

Referring again to FIG. 1, display devices 120 are configured for displaying, alarming, and/or basing medicament delivery on the sensor information that has been transmitted by the sensor electronics module 106 (e.g., in a customized data package that is transmitted to one or more of display devices 120 based on their respective preferences). Each of the display devices 120 can include a display such as a touchscreen display for displaying sensor information to a user (most often host 102 or a care taker/medical professional) and/or receiving inputs from the user. In some embodiments, the display devices 120 may include other types of user interfaces such as a voice user interface instead of or in addition to a touchscreen display for communicating sensor information to the user of the display device 120 and/or receiving user inputs. In some embodiments, one, some or all of the display devices 120 are configured to display or otherwise communicate the sensor information as it is communicated from the sensor electronics module 106 (e.g., in a data package that is transmitted to respective display devices 120), without any additional prospective processing required for calibration and real-time display of the sensor information.

In the embodiment of FIG. 1, one of the plurality of display devices 120 may be a custom display device 120a specially designed for displaying certain types of displayable sensor information associated with analyte values received from the sensor electronics module 106 (e.g., a numerical value and an arrow, in some embodiments). In some embodiments, one of the plurality of display devices 120 may be a handheld device 120c, such as a mobile phone based on the Android or iOS operating system, a palm-top computer and the like, where handheld device 120c may have a relatively larger display and be configured to display a graphical representation of the continuous sensor data (e.g., including current and historic data). Other display devices can include other hand-held devices, such as a tablet 120d, a smart watch 120b, a medicament delivery device 120e, a blood glucose meter, and/or a desktop or laptop computer.

As alluded to above, because the different display devices 120 provide different user interfaces, content of the data packages (e.g., amount, format, and/or type of data to be displayed, alarms, and the like) can be customized (e.g., programmed differently by the manufacture and/or by an end user) for each particular display device and/or display device type. Accordingly, in the embodiment of FIG. 1, one or more of display devices 120 can be in direct or indirect wireless communication with the sensor electronics module 106 to enable a plurality of different types and/or levels of display and/or functionality associated with the sensor information, which is described in more detail elsewhere herein.

Continuous Analyte Sensor

Continuous analyte sensor 108 of FIG. 1 may be, for example a subcutaneous, transdermal (e.g., transcutaneous), or intravascular device. In some embodiments, continuous analyte sensor 108 can analyze a plurality of intermittent blood samples, although continuous analyte sensor 108 can be configured to use any method of analyte-measurement, including enzymatic, chemical, physical, electrochemical, spectrophotometric, polarimetric, calorimetric, iontophoretic, radiometric, immunochemical, and the like.

Continuous analyte sensor 108 can use any known method, including invasive, minimally invasive, and non-invasive sensing techniques (e.g., fluorescent monitoring), to provide a data stream indicative of the concentration of a measured analyte in host 102. In some embodiments, this data stream is typically a raw data signal, which is converted into a calibrated and/or filtered data stream that is used to provide a useful value of the measured analyte to a user, such as host 102 or a caretaker (e.g., a parent, a relative, a guardian, a teacher, a doctor, a nurse, or any other individual that has an interest in the well-being of host 102). It should be understood that the devices and methods described herein can be applied to any device capable of detecting a concentration of an analyte and providing an output signal that represents the concentration of the analyte.

In some embodiments, continuous analyte sensor 108 may be capable of measuring a concentration of glucose in host 102, one of which is described below as utilizing an implantable continuous glucose sensor. For example, continuous analyte sensor 108 may be an implantable glucose sensor, such as described with reference to U.S. Pat. No. 6,001,067 and U.S. Patent Publication No. US-2005-0027463-A1. In another embodiment, continuous analyte sensor 108 may be a transcutaneous glucose sensor, such as described with reference to U.S. Patent Publication No. US-2006-0020187-A1. In still other embodiments, continuous analyte sensor 108 may be configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, co-pending U.S. Patent Publication No. US-2008-0108942-A1 filed on Mar. 26, 2007, and co-pending U.S. Patent Application No. US-2007-0197890-A1 filed on Feb. 14, 2007. In one alternative embodiment, continuous analyte sensor 108 comprises a transcutaneous sensor such as described in U.S. Pat. No. 6,565,509 to Say et al., for example. In another alternative embodiment, continuous analyte sensor 108 comprises a subcutaneous sensor such as described with reference to U.S. Pat. No. 6,579,690 to Bonnecaze et al. or U.S. Pat. No. 6,484,046 to Say et al., for example. In another alternative embodiment, continuous analyte sensor 108 comprises a refillable subcutaneous sensor such as described with reference to U.S. Pat. No. 6,512,939 to Colvin et al., for example. In another alternative embodiment, continuous analyte sensor 108 comprises an intravascular sensor such as described with reference to U.S. Pat. No. 6,477,395 to Schulman et al., for example. In another alternative embodiment, continuous analyte sensor 108 comprises an intravascular sensor such as described with reference to U.S. Pat. No. 6,424,847 to Mastrototaro et al., for example.

Figure 2A:
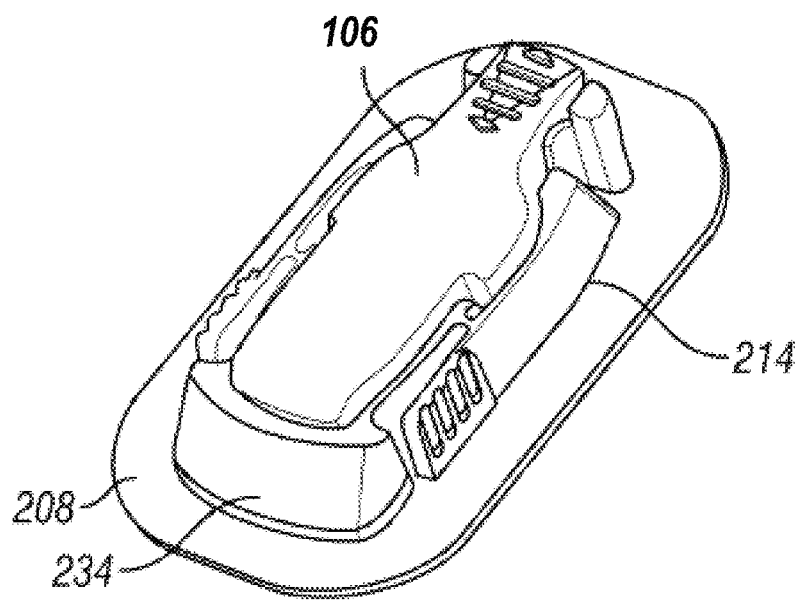
FIG. 2A is a perspective view of an example sensor electronics module of the example continuous analyte sensor system of FIG. 1.
Figure 2B:
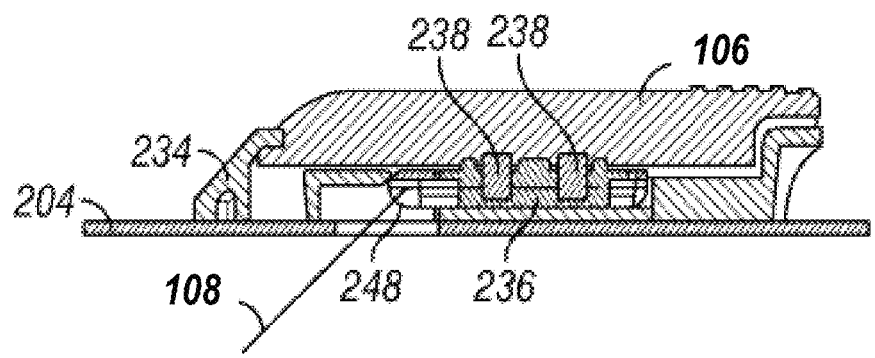
FIG. 2B is a side view of the example sensor electronics module of FIG. 2A.

FIGS. 2A and 2B are perspective and side views of analyte sensor system 104 shown in FIG. 1 according to certain aspects of the present disclosure. Analyte sensor system 104 may include a mounting unit 214 and sensor electronics module 106 attached thereto in certain embodiments, shown in its functional position, where mounting unit 214 and sensor electronics module 106 are matingly engaged therein. In some embodiments, the mounting unit 214, also referred to as a housing or sensor pod, comprises a base 234 adapted for fastening to a host's skin. The base 234 can be formed from a variety of hard or soft materials, and can have a low profile for minimizing protrusion of the device from the host during use. In some embodiments, the base 234 is formed at least partially from a flexible material, which can provide numerous advantages over conventional transcutaneous sensors that may suffer from motion-related artifacts associated with movement of the host when the host is using the device. The mounting unit 214 and/or sensor electronics module 106 can be located over a sensor insertion site to protect the site and/or provide a minimal footprint (i.e., utilization of the surface area of the host's skin).

In some embodiments, a detachable connection between the mounting unit 214 and sensor electronics module 106 is provided, enabling improved manufacturability. That is, mounting unit 214 (which may be relatively inexpensive) can be disposed of when replacing continuous analyte sensor 108 after its usable life, while the relatively more expensive sensor electronics module 106 can be reusable with additional, replacement continuous analyte sensors 108. In some embodiments, the sensor electronics module 106 is configured with signal processing (programming) functionality, for example, filtering algorithms, calibration algorithms, and/or other algorithms useful for calibration and/or the display of sensor information. However, an integral (non-detachable) sensor electronics module 106 is also contemplated for use in accordance with other embodiments.

In some embodiments, the contacts 238 are mounted on or in a subassembly hereinafter referred to as a contact subassembly 236 configured to fit within the base 234 of the mounting unit 214 and a hinge 248 that allows the contact subassembly 236 to pivot between a first position (for insertion) and a second position (for use) relative to the mounting unit 214. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, the contacts 238 are formed from a conductive elastomeric material, such as a carbon black elastomer, through which the continuous analyte sensor 108 extends.

In certain embodiments, the mounting unit 214 is provided with an adhesive pad 208, disposed on a back surface of mounting unit 214 and includes a releasable backing layer. Thus, removing the backing layer and pressing the base portion 234 of the mounting unit 214 onto the host's skin 204 adheres the mounting unit 214 to the host's skin 204. Additionally or alternatively, an adhesive pad can be placed over some or all of the analyte sensor system 104 after insertion of a continuous analyte sensor 108 is complete to ensure adhesion, and optionally to ensure an airtight seal or watertight seal around the wound exit-site (or continuous analyte sensor 108 insertion site) (not shown). Appropriate adhesive pads can be chosen and designed to stretch, elongate, conform to, and/or aerate the region (e.g., host's skin 204). The embodiments described with reference to FIGS. 2A and 2B are described in more detail with reference to U.S. Pat. No. 7,310,544, which is incorporated herein by reference in its entirety. Configurations and arrangements can provide water resistant, waterproof, and/or hermetically sealed properties associated with the mounting unit/sensor electronics module 106 embodiments described herein.

Various methods and devices that are suitable for use in conjunction with aspects of some embodiments are disclosed in U.S. Patent Publication No. US-2009-0240120-A1, which is incorporated herein by reference in its entirety for all purposes.

Figure 3:
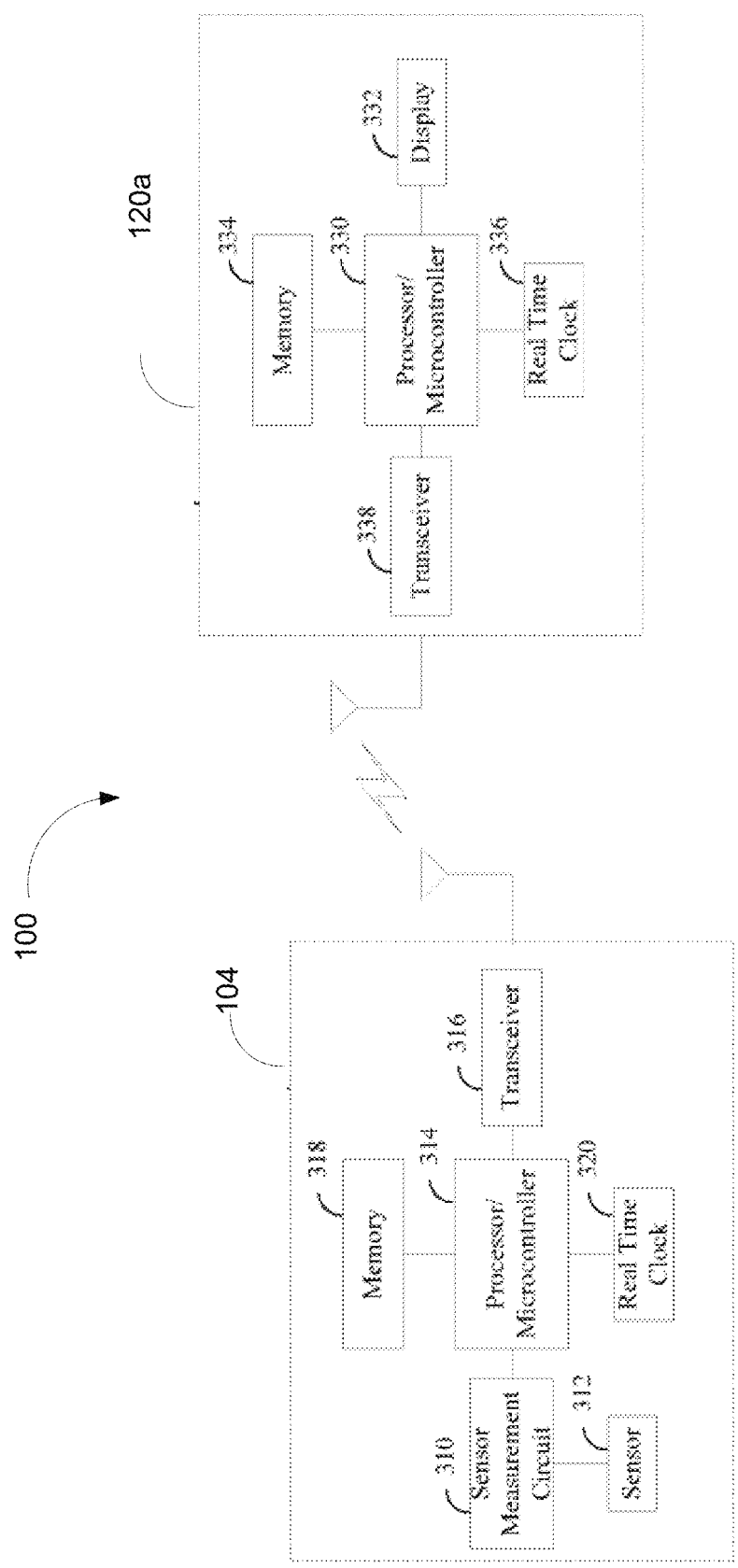
FIG. 3 is a block diagram illustrating elements of an example continuous analyte monitoring system and display devices in accordance with various embodiments described in the present disclosure.

FIG. 3 is a block diagram illustrating example components of analyte sensor system 104 and at least one of the plurality of display elements 120a, as well as the communications therebetween. The analyte sensor system 104 may include an implantable continuous analyte sensor 312 (one embodiment of continuous analyte sensor 108 of FIG. 1) coupled to a sensor measurement circuit 310 for processing and managing sensor data. The sensor measurement circuit 310 may be coupled to a processor 314 (part of sensor electronics module 106 in FIG. 1). In some embodiments, the processor 314 may perform part or all of the functions of the sensor measurement circuit 310 for obtaining and processing sensor measurement values from the implantable continuous sensor 312. The processor may be further coupled to a radio unit or transceiver 316 (part of sensor electronics module 106 in FIG. 1) for sending sensor information to and receiving requests and commands from an external device, such as display device 120a, which is used to display or otherwise provide the sensor information to a user. As used herein, the terms "radio unit" and "transceiver" are used interchangeably and generally refer to a device that can wirelessly transmit and receive data. The analyte sensor system 104 may further include a memory 318 (also part of sensor electronics module 106 in FIG. 1) and a real time clock (RTC) 320 (again, part of sensor electronics module 106 in FIG. 1) for storing and tracking sensor information.

Wireless communication protocols may be used to transmit and receive data between analyte sensor system 104 and display device 120a. The wireless communication protocol used may be designed for use in a wireless sensor network that is optimized for periodic and small data transmissions (that may be transmitted at low rates if necessary) to and from multiple devices in a close range (e.g., a personal area network (PAN)). For example, the wireless communication protocol may be optimized for periodic data transfers where transceivers may be configured to transmit data for short intervals and then enter low power modes for long intervals. The wireless communication protocol may have low overhead requirements both for normal data transmissions and for initially setting up communication channels (e.g., by reducing header overhead) to reduce power consumption. In some embodiments, burst broadcasting schemes (e.g., one way communication) may be used. This may eliminate overhead required for acknowledgement signals and allow for periodic transmissions that consume little power.

The wireless communication protocol may further be configured to establish communication channels with multiple display devices, e.g., two or more of display devices 120, while implementing interference avoidance schemes. In some embodiments, the wireless communication protocol may make use of adaptive isochronous network topologies that define various time slots and frequency bands for communication with several ones of display devices 120. The wireless communication protocol may thus modify transmission windows and frequencies in response to interference and to support communication with multiple ones of display devices 120. Accordingly, the wireless protocol may use time and frequency division multiplexing (TDMA) based schemes. The wireless communication protocol may also employ direct sequence spread spectrum (DSSS) and frequency-hopping spread spectrum schemes. Various network topologies may be used to support short-distance and/or low-power wireless communication such as peer-to-peer, start, tree, or mesh network topologies such as WiFi, Bluetooth and Bluetooth Low Energy (BLE). The wireless communication protocol may operate in various frequency bands such as an open ISM band such as 2.4 GHz. Furthermore, to reduce power usage, the wireless communication protocol may adaptively configure data rates according to power consumption.

Display device 120a may be used for alerting and providing sensor information to a user, such as host 102, and may include a processor 330 for processing and managing sensor information. Display device 120a may include a display 332, a memory 334, and a real time clock 336 for displaying, storing and tracking sensor information, respectively. Display device 120a may further include a radio unit or transceiver 338 for receiving sensor information and for sending requests, instructions, and data to the analyte sensor system 104. The transceiver 338 may further employ a wireless communication protocol. The memory 334 may also be used for storing an operating system and/or a custom (e.g., proprietary) application designed for wireless data communication between a transceiver, e.g., transceiver 316 and display device 120a. The memory 334 may be a single memory device or multiple memory devices and may be a volatile or non-volatile memory for storing data and/or instructions for software programs and applications. The instructions may be executed by the processor 330 to control and manage the transceiver 338.

It should be understood that in the case of display device 120e, which may be a medicament delivery device in addition to or instead of a display device, the alerts and/or sensor information provided by continuous analyte sensor 108 vis-à-vis sensor electronics module 106, can be used to initiate and/or regulate the delivery of the medicament to host 102.

In some embodiments, when a standardized communication protocol is used, commercially available transceiver circuits may be utilized that incorporate processing circuitry to handle low level data communication functions such as the management of data encoding, transmission frequencies, handshake protocols, and the like. In these embodiments, processors 314 and 330 do not need to manage these activities, but rather provide desired data values for transmission, and manage high level functions such as power up or down, set a rate at which messages are transmitted, and the like. Instructions and data values for performing these high level functions can be provided to the transceiver circuits 316 and 338, respectively, via a data bus and transfer protocol established by the manufacturer of the transceiver circuits 316 and 338.

Components of the analyte sensor system 104 may require replacement periodically. For example, implantable continuous analyte sensor 312 that may be attached to sensor electronics module 106 which itself includes the sensor measurement circuit 310, the processor 314, memory 318, and transceiver 316, and battery (not shown) may require periodic replacement (e.g., every 7-30 days). The sensor electronics module 106 may be configured to be powered and active for much longer than implantable continuous analyte sensor 312 (e.g., for 3 months, 6 months or more) until the battery needs replacement. Replacing these components may be difficult and require the assistance of trained personnel. Reducing the need to replace such components, including the battery if replaceable, significantly improves the convenience of the analyte sensor system 104 to the host 102.

When sensor electronic module 106 is used for the first time (or reactivated once a battery has been replaced in some cases), it may be connected to implantable continuous analyte sensor 312. As will be further described below, there may be a process for initially establishing communication between display device 120a and sensor electronics module 106 when it is first used or re-activated (e.g., the battery is replaced). Once display device 120a and sensor electronics module 106 have established communication, display device 120a and sensor electronics module 106 may periodically and/or continuously be in communication over the life of several ones of implantable continuous analyte sensor 312 until, for example, the battery or the entirety of sensor electronics module 106 needs to be replaced. Each time continuous analyte sensor 312 is replaced, notifications of a new continuous analyte sensor 312 can be sent/exchanged via the previously established communication between the sensor electronics module 106 and display device 120a.

In accordance with one embodiment, analyte sensor system 104 gathers and processes analyte measurements from continuous analyte sensor 312, and periodically sends sensor information representative of the analyte measurements to display device 120a. Measurements are gathered and transmitted over the life of continuous analyte sensor 312 (e.g., in the range of 1 to 30 days or more). New measurements may need to be transmitted often enough to adequately monitor analyte levels. Rather than having the transmission and receiving circuitry of each of the analyte sensor system 104 and display device 120a continuously communicating, the analyte sensor system 104 and display device 120a may regularly and periodically establish a communication channel between them. Thus, analyte sensor system 104 can communicate wirelessly with display device 120a at predetermined time intervals. The duration of the predetermined time interval can be selected to be long enough so that the analyte sensor system 104 does not consume too much power by transmitting data more frequently than needed, yet frequent enough to provide substantially real-time sensor information (e.g., measured analyte values) to one or more of display devices 120 for output (e.g., display) to a user. While the predetermined time interval is every five minutes in some embodiments, it is appreciated that this time interval can be varied to be any desired length of time. It should be noted that other contemplated embodiments involve irregular or aperiodic transmissions of sensor information, e.g., from analyte sensor system 104 to one or more of display devices 120.

Figure 4:
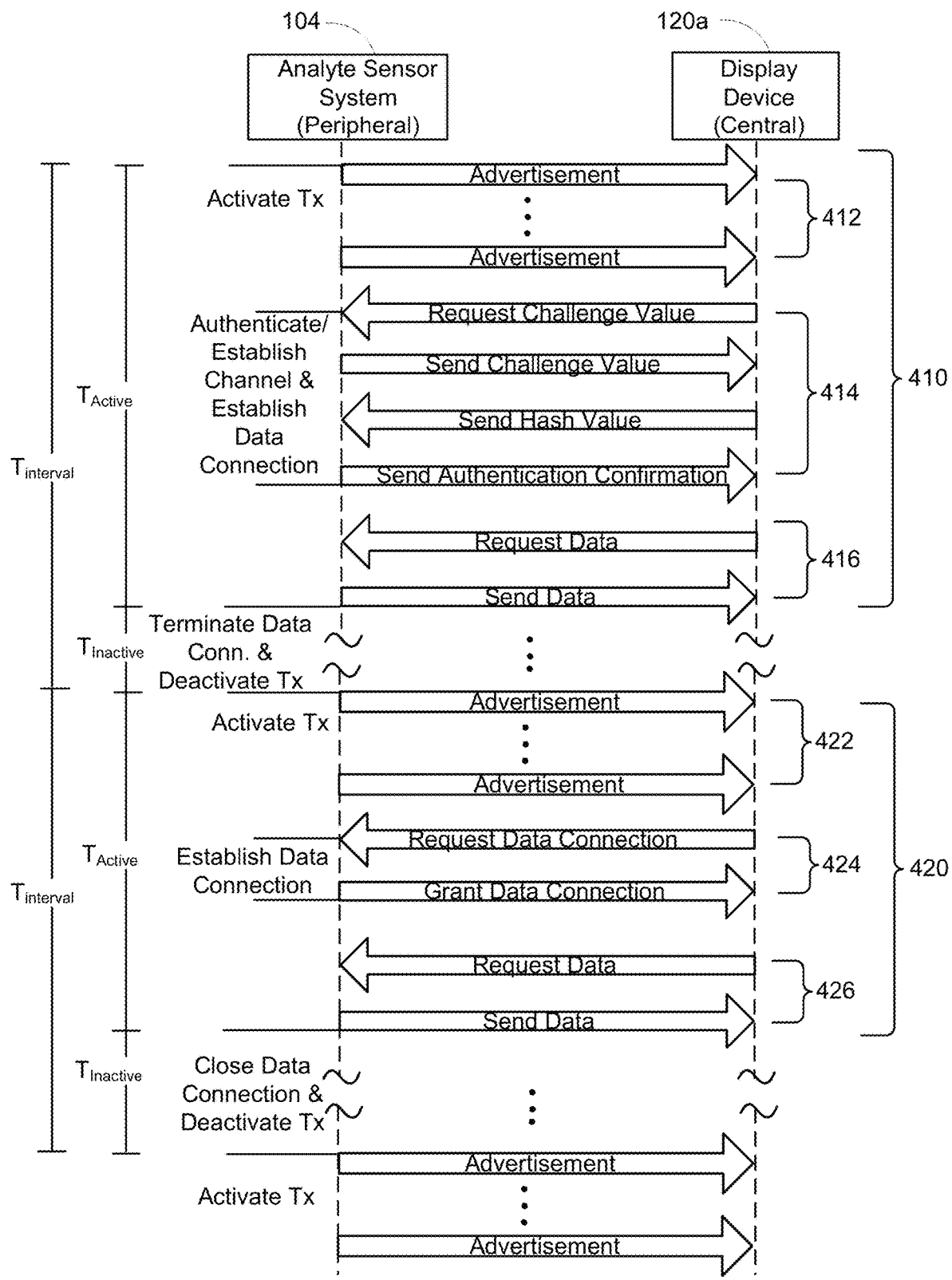
FIG. 4 is an example advertising/connection sequence in accordance various embodiments described in the present disclosure.

FIG. 4 is an example advertising/connection sequence between analyte sensor system 104 and display device 120a which is capable of wirelessly receiving analyte measurement values from the analyte sensor system 104 according to certain aspects of the present disclosure. The various tasks performed in connection with the advertising/connection illustrated in FIG. 4 may be performed by a processor executing instructions embodied in a non-transitory computer-readable medium. For example, the tasks performed in connection with the procedure may be performed by hardware, software, firmware, or any combination thereof incorporated into one or more of computing devices, such as analyte sensor system 104 and display device 120a of FIG. 1 and/or FIG. 3. It should be appreciated that the procedure may include any number of additional or alternative tasks. The tasks shown in FIG. 4 need not be performed in the illustrated order, and the procedure may be incorporated into a more comprehensive procedure or process having additional functionality not described in detail herein.

In the example described below, the analyte values are glucose values based on one or more measurements of glucose levels by the implantable continuous analyte sensor 312 for illustration purposes. However, it should be understood that the analyte values can be any other analyte value described herein. The wireless data communication between the analyte sensor system 104 and the display device 120a may happen periodically, at times separated by an update interval denoted "$T_{interval}$" that may correspond to a time duration between two consecutive wireless communication sessions between the transceiver 316 of the analyte sensor system 104 and the transceiver 338 of display device 120a. Alternatively, the update interval may be thought of as a period of obtaining and sending a recently measured glucose value. Transmitting advertisement signals, establishing a data connection (e.g., a communication channel) and requesting and sending data may occur during wireless communication sessions each lasting an active time or period denoted "$T_{Active}$" within an update interval $T_{interval}$. In between two consecutive wireless communication sessions, the transceiver 316 goes into an inactive or sleep mode for an inactive period denoted as "$T_{Inactive}$" to conserve battery life and/or reduce peak voltage requirements, for example.

FIG. 4 shows two such wireless communication sessions, namely, a first wireless communication session 410 and a second wireless communication session 420. Each wireless communication session 410, 420 starts with the analyte sensor system 104 establishing a data connection with display device 120a. To establish a data connection with display device 120a, the transceiver 316 of the analyte sensor system 104 transmits a series of advertisement signals 412 during the first wireless communication session 420. Each advertisement signal may be considered an invitation for display device 120a to establish a data connection with the transceiver 316. In some embodiments, advertisement signals 412 may be embodied as advertising beacons, as will be discussed in greater detail below.

In the illustrated example of FIG. 4, it is assumed that the analyte sensor system 104 needs to engage in an initial system setup because the analyte sensor system 104 has been just turned on for the first time and/or is not current paired with display device 120a. Typically, a user of display device 120a identifies a new or never-been used analyte sensor system 104 that needs to be paired with display device 120a by entering identification information (e.g., a serial number) associated with the new/unpaired analyte sensor system 104 via a custom application running on display device 120a using a user interface (e.g., a touchscreen display). During the first wireless communication session 410, an authentication procedure can be performed as part of a data connection process 414. To establish a data connection with the analyte sensor system 120, the display device 120a listens continuously until an advertisement signal transmitted by the transceiver 316 of the analyte sensor system 104 is received. Once the transceiver 316 begins transmitting advertisement signals 412, it may take one, two, or more advertisement signals for the display device 120a to receive at least one of the advertisement signals and respond to at least one of the advertisement signals. In some embodiments, the transceiver 316 stops sending additional advertisement signals once display device 120a receives an advertisement signal and responds to that advertisement signal, for example, via an acknowledgement. In other embodiments, the transceiver 316 may continue to send additional advertisement signals even after receiving a response from display device 120a so that another display device, e.g., one or more of display devices 120b-e, may receive and respond to at least one of the additional advertisement signals. After an advertisement signal is successfully received by display device 120a, display device 120a and the analyte sensor system 104 engage in a first data connection process 414. During the first data connection process 414, the display device 120a requests a challenge value from the analyte sensor system 104 and the analyte sensor system 104 sends the change value to the display device 120a in response. Upon receiving the challenge value, the display device 120a calculates a hash value based on the challenge value and the identification information associated with the analyte sensor system 104 and/or the transceiver 316 and sends the hash value to the transceiver 316. The transceiver 316 receives the hash value from the display device 120a, decodes the identification information from the hash value, and verifies that the received identification information matches identification information associated with the analyte sensor system 104 and/or transceiver 316 previously stored in the memory 318 of the analyte sensor system 104, such as during manufacturing of the analyte sensor system 104. Upon verification, the transceiver 316 sends a signal confirming a successful authentication to the display device 120a. Once authenticated, the analyte sensor system 104 and display device 120a may exchange information to determine how data will be exchanged (e.g., a specific frequency, time slot assignment, encryption, etc.).

After completion of the first data connection process 414, the analyte sensor system 104 and now-connected display device 120a engage in a first data communication 416 during which display device 120a requests and receives desired information (e.g., analyte measurement data, control information, identification information, and/or instructions) from the analyte sensor system 104. When the first data communication 416 is completed, the data connection is terminated (e.g., by closing the established communication channel) and the transceiver 316 and/or the processor 314 of the analyte sensor system 104 (and possibly the transceiver 338 and/or the processor 330 of the display device 120a as well, depending on implementation preference) can be deactivated by causing the transceiver 316 and/or the processor 314 to enter a sleep or inactive mode. In some embodiments, the transceiver 316 is completely powered down during a sleep mode. In other embodiments, the transceiver 316 is in a low power mode using only a small fraction (e.g., 1-10%) of the normal current/power. As will be discussed further below, transceiver 316 may be woken up, for example, by an NFC on-demand request from one of display devices 120 for sensor information to be sent to another one of display devices 120, e.g., display device 120a, accelerometer movement that triggers a wake up of transceiver 316, etc. It should be noted that in some embodiments, advertising signals themselves can have specific headers so that directed or targeted advertising can be performed. For example, one of display devices 120 listed in a whitelist (discussed in greater detail below) may not respond to advertising signals unless the advertising signals are directed specifically to that display device.

The active period $T_{Active}$ corresponding to a duration of each wireless communication session may be a small fraction of the update interval $T_{interval}$ corresponding to a period between two consecutive wireless communication sessions. For example, $T_{interval}$ may be between about 200 and 400 seconds and $T_{Active}$ may be between 20 and 40 seconds. As such, the transceiver 316 of the analyte sensor system 104 may be powered fully for only 10 percent (e.g., 30 seconds) of a five minute $T_{interval}$. This may significantly reduce power consumption and peak voltage demand. In some cases, the transceiver 316 is not completely powered down, but enters a low-power mode when not transmitting. After an inactive time or period $T_{Inactive}$, a second wireless communication session 420 starts when the transceiver 316 (and the transceiver 338) powers up again, begins transmitting a second series of advertisement signals 422, engages in a second data connection process 424 and a second data communication process 426 with the transceiver 338 of display device 120a as shown in FIG. 4. Unlike the first data connection process 414, however, the second data connection process 424 need not involve an authentication procedure because the analyte sensor system 104 and the display device 120a have been successfully paired or bonded during the first wireless communication session 410 as described above. This process may continue, with new data connections and communications being completed at the predetermined intervals. During all or part of each inactive period $T_{Inactive}$ during which the transceiver 316 is in a sleep mode, the processor 314 can take measurement(s) of one or more analyte values using the analyte sensor 312 and the sensor measurement circuitry 310. For example, the processor 314 may take multiple analyte value measurements and average them to generate a single averaged analyte value to be transmitted in a next wireless communication session.

Continuously re-establishing a new communication channel to allow for partially or wholly powering down the transceiver 316 during each update interval $T_{interval}$ can provide significant power savings and can allow the sensor electronics module 106 (FIG. 1) to operate continuously for, e.g., 1 month, 3 months, 6 months, 1 year, etc., without requiring a battery replacement. It should be noted that in some embodiments, battery replacement may be a function of the actual expiration of battery power or some predetermined level of remaining battery power. Furthermore, rather than blindly transmitting glucose data points during the update interval $T_{interval}$, establishing specific data connections (e.g., communication channels) with only desired display devices, e.g., display device 120a, can prevent unauthorized use and interception of glucose measurement values. In some embodiments, only a subset of multiple display devices 120 can be configured to receive different data such as glucose measurement values and/or alarm conditions. For example, in addition to a display device identifier(s), a whitelist may be populated with a data type identifier indicative of a type of data to be sent to that particular display device(s) populating the whitelist. In other embodiments, the sensor electronics module 106 may be pre-programmed with preference or profile information, which can be accessed to determine what type(s) of data are to be sent to what display device(s). Thus, prior to the exchange of sensor information, the sensor electronics module 106, for example, can access the whitelist (or bonding list in some embodiments) and/or preference/profile information to determine what type(s) of data should be sent to a display device. In still other embodiments, initial communications between sensor electronics module 106 and a display device, the display device can transmit type information to sensor electronics module 106. This has a benefit of preventing all of display devices 120 from issuing alarms, thereby confusing and/or frustrating the user. In addition, by establishing a secure two-way communication channel, requests for specific glucose measurement values or communication of calibration or configuration information may be transmitted on an as-needed/requested basis between the analyte sensor system 104 and display device 120a.

Also, in some embodiments, the transceiver 316 may not be activated for data communication every update interval $T_{interval}$. Instead, the transceiver 316 may be activated every second, third or fourth update interval $T_{interval}$, for example, so that communication between the analyte sensor system 104 with the display device 120a occurs less frequently than every update interval $T_{interval}$. Doing so can further reduce power consumption. Activation could also depend on the sensor information. For example, the transceiver 316 need only be activated if data meets certain thresholds, such as a current rate of change, current high value, current low value, absolute difference from a previously exchanged value, percentage difference from a previously exchanged value, and the like. In some embodiments, instead of skipping certain fixed update intervals, the length of each interval can be made to vary based on the sensor information or other criteria. For example, if the sensor information indicates a low glucose value and/or a hypoglycemic reaction is detected, the update interval value can be shortened from a normal (longer) update interval value so that more frequent readings are taken and/or transmitted.

In some embodiments, one or more of the update interval $T_{interval}$, the active period $T_{Active}$ and a frequency $F_{Activation}$ by which the transceiver is activated (e.g., every second, third or fourth update interval) may be variable. In certain embodiments, the above-identified parameters can be user configurable (e.g., by inputting a value for the variable using user interface of display device 120a) and/or automatically varied by the analyte sensor system 104 or display device 120a based on one or more criteria. The criteria can include: (i) a monitored battery power of the sensor system 104, (ii) a currently measured, previously measured and/or predicted glucose concentrations meeting or exceeding a predetermined threshold, (iii) a glucose concentration trend of the host based on currently measured, previously measured and/or predicted glucose concentrations, (iv) a rate of change of glucose concentration of the host based currently measured, previously measured and/or predicted glucose concentrations meeting or exceeding a predetermined threshold, (v) whether the host is determined to be in or near hyperglycemia based on currently measured, previously measured and/or predicted glucose concentrations, (vi) whether the host is determined to be in or near hypoglycemia based on currently measured, previously measured and/or predicted glucose concentrations, (vii) user inputted activity of the host (e.g., exercising or sleeping), (viii) time since a sensor session has started (e.g., when a new sensor 10 is used), (ix) one or more errors detected by sensor system 104 or display device 120a and (x) type of display device 120a (where the display device 120a can be connected or populating the whitelist or bonding list).

$T_{interval}$, $T_{Active}$, $F_{Activation}$ and/or other configuration items described herein may form part of a communication protocol profile that may be stored on any device that implements the fundamental communication protocol to allow for a customized use of the protocol for communicating analyte measurement values in the analyte sensor system 104 and one or more of display devices 120.

Power Savings and Connection Reliability

As discussed above, reducing the need to replace components significantly improves the convenience of the analyte sensor system 104 to the user. Accordingly, various embodiments are directed to power saving schemes and/or mechanisms to increase battery life of analyte sensor system 104, e.g., sensor electronics module 106. Although generalized concepts of putting a transceiver, such as transceiver 316, into a sleep or low power mode, and continuously re-establishing a new communication channel to allow for partially or wholly powering down transceiver 316 have been described, specific parameters or variables for communicating as well as conditions for dictating how those specific parameters or variables are adjusted will be further discussed below. The result of adjusting such parameters or variables as governed by certain communication conditions are efficient systems and methods for initiating or requesting communications (intelligent advertising) as well as transmitting data (intelligent communications).

Still another result of the adjustment of parameters and variables in response to communication conditions is increased connection reliability between analyte sensor system 104, e.g., sensor electronics module 106, and one or more of display devices 120. For example, and in the context of advertising, advertising variables can be set or selected based on some minimum reliability to avoid or lessen the occurrence of missed advertising beacons when the advertising interval is short (to avoid excessive battery drain on sensor electronics module 106 as a result of longer advertising intervals). Thus, the optimizing of communications is in and of itself an advantage realized by various embodiments beyond the increase in power savings.

Radio Software and Architecture

From a radio design/implementation perspective, the radio software and architecture utilized to implement various embodiments are configured in accordance with intelligent advertising and communication considerations. Accordingly, various embodiments implement radio software based on background and foreground processing for application control, where the foreground processing can be referred as "main-loop" processing, which manages wireless connections and passing data within sensor electronics module 106 using four commands with sleep (low power mode) support. The four commands include "start communication," "stop communication," "CGM receive," and "CGM transmit" and will be described in greater detail below.

Figure 5:
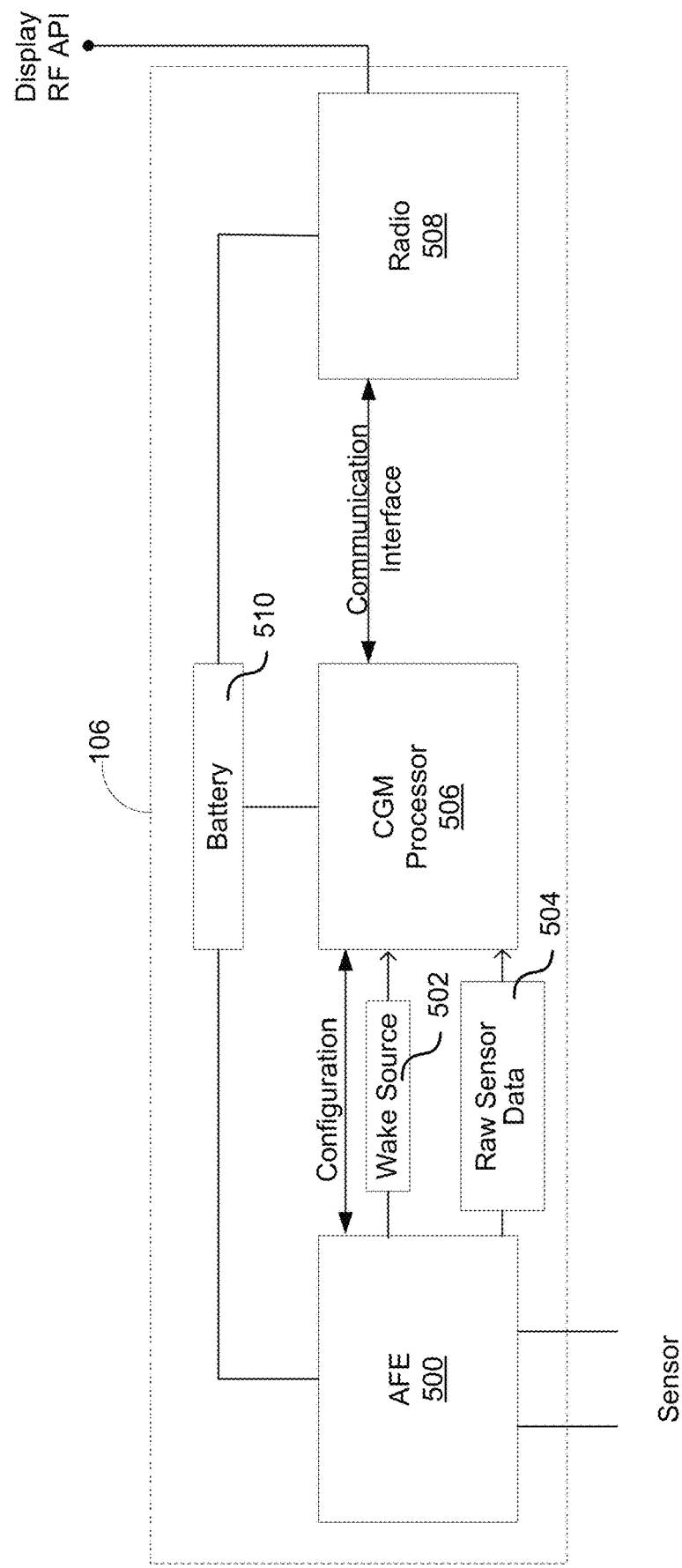
FIG. 5 is a block diagram illustrating various elements involved in the transmission of data from an example continuous analyte monitoring system in accordance with various embodiments described in the present disclosure.

FIG. 5 is a block diagram illustrating various elements of sensor electronics module 106 (of FIG. 1) involved in the transmission of sensor information in a continuous analyte monitoring system 100 in accordance with various embodiments described in the present disclosure. It should be noted that the following embodiments are described in the context of a continuous glucose monitoring (CGM) system (an embodiment of continuous analyte monitoring system 100), where one example wireless communication protocol used for communications between analyte sensor system 104 and one or more of display devices 120 is the Bluetooth® Low Energy (BLE) standard. However, it should be understood that other continuous analyte monitoring systems and other transceivers or radios may be utilized such as those operating in accordance with other low power/short-range communications protocols.

After startup or powering on of sensor electronics module 106, a radio 508 is initialized and may enter a "sleep mode" waiting for a command from a CGM processor 506. It should be appreciated that radio 508 may be an embodiment of transceiver 316 (FIG. 3), CGM processor 506 may be an embodiment of processor 314, and the sleep mode may refer to one of the inactive periods $T_{inactive}$ described with reference to FIG. 4. An Analog Front End (AFE) 500 initializes to its default state and also waits for configuration commands.

Figure 6:
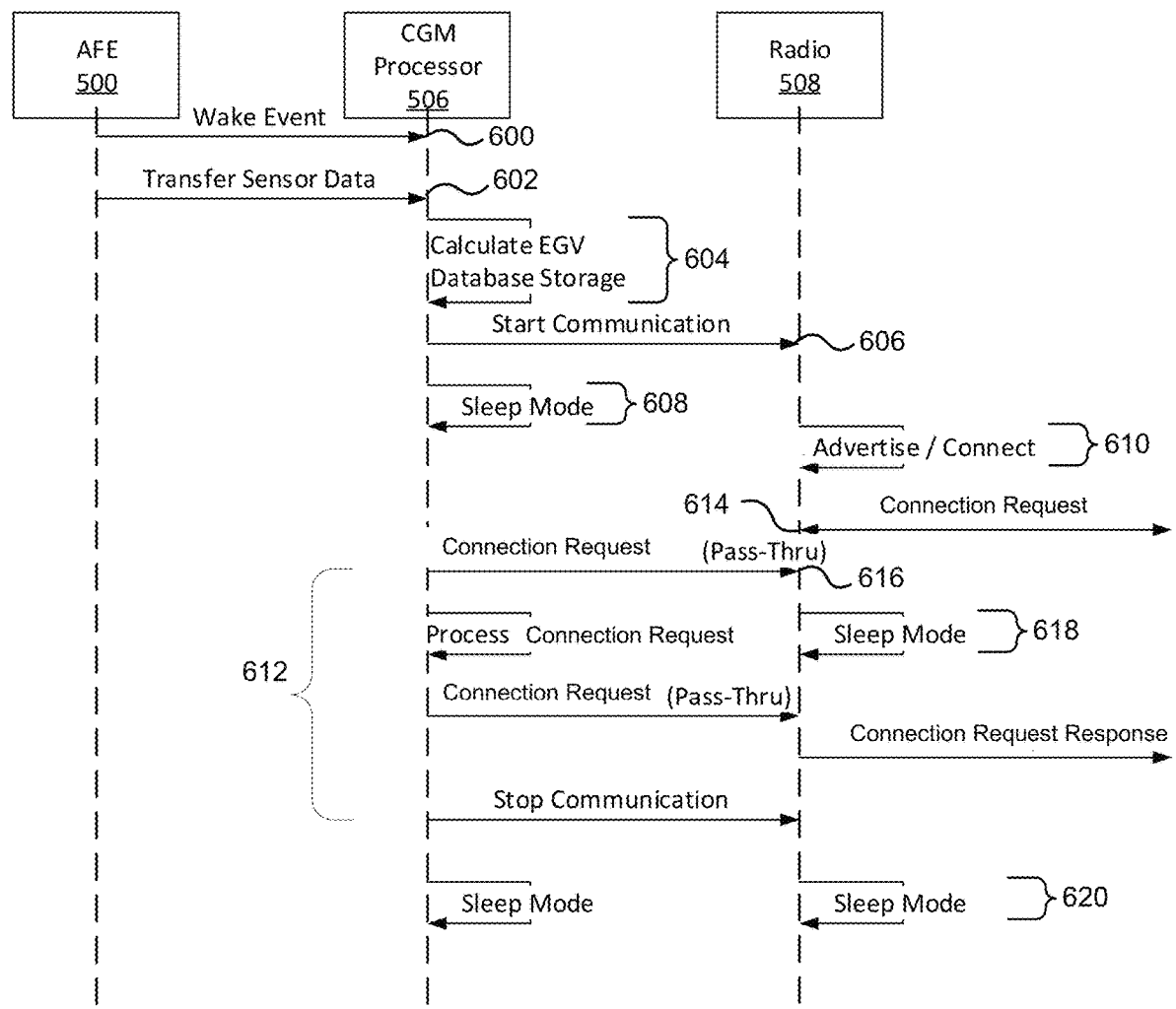
FIG. 6 is an example transmitter processing/command sequence in accordance with various embodiments described in the present disclosure.

FIG. 6 illustrates an example transceiver processing/connection sequence which will be described in conjunction with the elements of sensor electronics module 106 shown in FIG. 5. Whereas FIG. 4 and its corresponding description provide a broader description of wireless communications between analyte sensor system 104 and display device 102a, FIG. 6 describes the wireless communications from a more detailed perspective of the one or more components comprising sensor electronics module 106.

As illustrated in FIG. 6, radio 508 is operative to transmit advertisements (e.g., advertisements 412 of FIG. 4). Such advertisements may comprise small packets of data broadcast at, e.g., regular intervals. In particular, advertising may be a one-way communication method, where system elements that want to be discovered (such as display devices, when analyte sensor system 104 wishes to send sensor information to be displayed on at least one display device 120) broadcasts advertisement beacons or packets in predetermined intervals. Upon receipt of such advertisements, at least one of display device 120 can establish communications with analyte sensor system 104 (data connection process 414 of FIG. 4) to receive sensor information, for example, and display the sensor information (e.g., analyte and/or estimated glucose values), initiate an alarm, etc.

CGM processor 506, as described above, may be one embodiment of the aforementioned processor 314, which can take a measurement(s) of one or more analyte values, in this example, glucose values, using implantable continuous analyte sensor 312 and sensor measurement circuitry 310 or AFE 500. For example, CGM processor 506 may take multiple glucose value measurements and process the multiple glucose value measurements (e.g., via one or more processing algorithms, noise filters, etc.) to arrive at one or more transformed glucose values to be transmitted via radio 508. Moreover, AFE 500 may be one or more sets of analog signal conditioning circuitry utilizing, e.g., operational amplifiers, filters, ASICs, and/or other circuitry to allow the sensor to interface with CGM processor 506.

In accordance with some embodiments, staged task processing may be utilized to limit the run-time of processors (i.e., CGM processor 506 and radio 508) to avoid overlapping as much as possible, thereby reducing stress on the battery (and minimizing asynchronous messaging issues). In particular, and after initialization, AFE 500 samples raw sensor data 504 for, e.g., 5 minutes, while CGM processor 506 and radio 508 are in low power mode (a $T_{inactive}$ period of FIG. 4). Once AFE 500 is ready, a wake event is triggered by sending a "wake up" message to CGM processor 506 (process 600) causing the processor 506 to be awake, and during which raw sensor data transfer between AFE 500 and CGM processor 506 can be completed (process 602). AFE 500 may then return to low power mode acquisition of raw sensor data, for example. CGM processor 506 then calculates and stores estimated glucose value (EGV) data (process 604). CGM processor 506 may signal radio 508 to "start communication," (process 606) after which CGM processor 506 enters low power mode (process 608).

The start communication command is the first command radio 508 sees and can include data such as a transmitter ID, a communication interval, system mode, RTC value, and API version. Sending such data with each start command allows radio 508 to reset without having to issue an asynchronous command for configuration data. It also allows CGM processor 506 to control the state of radio 508 dynamically (i.e. setting storage mode). Once the start communication command is acknowledged, CGM processor 506 enters low power mode. It should be noted that CGM processor 506 can be designed to stay in sleep mode until real-time events and data processing is complete, thus minimizing main loop processing current draw to save battery power.

Radio 508 may begin advertising, and if one of display devices 120, e.g., display device 120a, creates a radio frequency (RF) link (process 610) (i.e., a wireless communication session is initiated and established per the transmission of advertisement signals 412 and data connection establishment 414 of FIG. 4), display device 120a and CGM processor 506 exchange commands/data (processes 612, also referred to as, e.g., first data connection 416, second data connection 426, etc. of FIG. 4). It should be noted that when display device 120a (not shown in FIG. 6) is connected, sensor electronics module 106 enters a "connection request mode," the purpose of which is to remove the asynchronous messaging complexity from the RF communication link. This connection request mode can be implemented using, e.g., control point/indication responses of the wireless communication protocol being utilized. Moreover, a connection request/response protocol may be used for all messages, where display device 120a only issues connection requests, and radio 508 only issues connection responses. Moreover, radio 508 may be placed in a connection "pass-thru" mode, using a message transport layer, and CGM processor 506 may process the appropriate connection (processes 614, 616). When display device 120a has an active RF communication link, both the CGM application and radio application are in low power mode. The radio stack keeps the RF communication link open, and only when a connection request is sent from display device 120a, will the radio/CGM applications exit low power mode.

In particular, a CGM receive command is triggered when the display devices sends a connection request on the wireless communications protocol API. This command takes the payload and sends it to CGM processor 506. In some embodiments, the payload is 20 bytes and any extra room is used to send real-time radio status data to CGM processor 506 for every command received. As described previously, the content of data packages, for example, can be customized depending on the display device type. Thus, in some embodiments, an indication of the type of display device that is active (currently engaged in data communications with analyte sensor system 104) can be provided in the payload. A CGM transmit command comprises a response to a display command request for performing the reverse operations of the CGM receive command, i.e., it takes the payload and sends it to the radio stack to be transmitted on the RF link. A stop communication command may be used to ensure radio 508 does not exceed a predefined "communication window," which in some embodiments is, e.g., 30 seconds, since RF noise can affect AFE sensor measurements. This stop command accordingly can be sent, e.g., 26 seconds after the start communication command is sent.

It should be further noted that radio 508 may also enter low power mode while CGM processor 506 is processing the connection request (process 618) and there are no main loop tasks to process. Once the display device 102a and CGM processor 506 complete the exchange of commands/data, both CGM processor 506 and radio 508 can enter low power mode (process 620 and also referred to as a $T_{inactive}$ period of FIG. 4).

Battery Life

As previously discussed, various embodiments are directed to maximizing/preserving battery life. To that end, sensor electronics module 106 is configured to operate in two low power modes, a storage mode and an active mode, with a wake source being utilized to wake sensor electronics module 106 from low power mode.

Storage mode (also referred to as shelf mode) is a mode in which sensor electronics module 106 is placed before being packaged. In accordance with one embodiment, sensor electronics module 106 can stay in this mode until it detects a sensor has been inserted and, at that time, automatically enters active mode. Storage mode places radio 508 in "deep sleep" as well as places CGM processor 506 into a no-clock mode to keep battery power consumption to absolute minimum levels. Active mode also implements a low power mode, but leaves the real-time clock active. This results in current being drawn, but allows CGM processor 506 to keep accurate time. Wake source 502 is a periodic event that wakes sensor electronics module 12 from low power mode and triggers it to start processing. Wake source 502 is typically provided by AFE 500, and this event first wakes up CGM processor 506 to configure system hardware and software to transfer raw sensor data 504.

Certain wireless communication protocols, such as the aforementioned BLE protocol, use a client/server model. For example, sensor electronics module 106 (including radio 508), also referred to as a peripheral, may act as a server while a display device (e.g., display device 120a), also referred to as a central, acts as a client. The peripheral makes advertisements as described above (e.g., 412, 422 of FIG. 4), while the central scans for advertisements. This model can operate using the concept of a Generic Attribute Profile (GATT) which defines how a server and client transfer data back and forth based on "services" (breaking up data into logic entities that contain data referred to as "characteristics") once a data connection has been established.

Advertising/Connection Protocol

In accordance with various embodiments, an advertising and connection protocol may be used to control how often and/or when sensor electronics module 106 (the peripheral) advertises for and connects to one or more display devices 120 (the central(s)). The advertising and connection protocol can allow for many different advertisement/connection scenarios. For example, the advertising and connection protocol can: advertise for and connect to a single central at a time; advertise for a plurality (e.g., two) centrals on each communication interval; and connect to a plurality of unique types of centrals on each communication interval. A connection order priority can be implemented for the different types of centrals, where each type of central may have a unique advertising interval and/or timeout period as will be discussed in greater detail below.

The advertising and connection protocol may utilize "clear text data exchange" as well as "encrypted data exchange." Moreover, the advertising and connection protocol may include various categories or modes of advertising. One mode can be referred to as general advertising, another mode can be referred to as whitelist advertising, and still another mode can be referred to as directed advertising. General advertising refers to a mode where any central can connect with the peripheral, whereas whitelist advertising refers to a mode of advertising in which all connection requests from centrals to the peripheral may be denied except for a connection request from a targeted central. Directed advertising may occur if a user wishes to request that the peripheral transmit sensor information to a desired central, e.g., in the case of a NFC-enabled display device 120c "tapping" analyte sensor system 104 to request a connection therebetween.

During general advertising, the whitelist may be empty, and populated with, e.g., a Generic Access Profile (GAP) Address or an Identity Resolving Key (IRK) entry upon a display device, i.e., a dedicated display device 120a, sending its configuration during a bonding exchange when a wireless connection is being established. It should be noted that the whitelist can be dynamically updated to reflect a desired priority for advertising and connection. For example, processor 314 of FIG. 3 can store connection statistics or history in memory 318 such that a certain one of display devices 120 is preferred over another based on time, location, and/or other considerations. The whitelist can also be dynamically updated based upon most recent connections. That is, bonded devices maintained in the bonding list and be filtered in accordance with the historical statistics and/or recent connections information to create the whitelist.

Figure 7A:
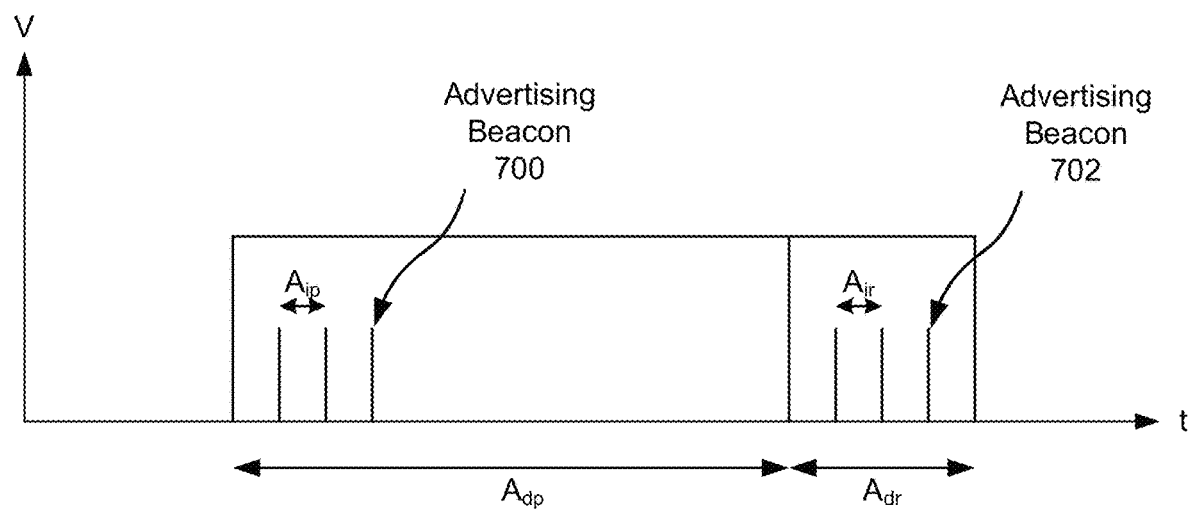
FIG. 7A is an example advertising profile in accordance with various embodiments described in the present disclosure.

FIG. 7A illustrates an example advertising sequence or profile associated with the advertising and connection protocol. As discussed above, radio 508 may be in low power mode when CGM processor 506 is woken up via wake source 502. CGM processor 506 may then transmit raw sensor data 504 from AFE 500, apply one or more algorithms to create/calculate an EGV value, and store that EGV value in memory, e.g., flash database. At this point, advertising can begin and CGM processor 506 can signal radio 508 to start advertising (e.g., 3 seconds after the wake event).

Radio 508 may advertise to one or more display devices/centrals, e.g., a handheld mobile device or a dedicated receiver, such as a CGM display device. As illustrated in FIG. 7A, radio 508 may send first advertising beacons 700 (also referred as advertisement signals 412 in FIG. 4) at a certain interval referred to as an advertising interval, $A_{ip}$, e.g., 90 ms. Such advertising beacons 700 are sent according to the advertising interval $A_{ip}$ for a predetermined time referred to as an advertising duration, $A_{dp}$. The advertising duration $A_{dp}$ is considered to be an amount of time radio 508 will transmit advertising beacons to one or more of display devices 120. In this example, the advertising duration $A_{dp}$ for a handheld device such as display device 120c may be 7 seconds. In the event a connection is made, advertising will end so that a wireless connection can be established. Radio 508 may also send second advertising beacons 702 to advertise to the CGM display device, e.g., display device 120a. Again, advertising beacons 702 are transmitted in accordance with a particular advertising interval, $A_{ir}$, which can be the same or different than advertising interval $A_{ip}$, for some advertising duration $A_{dr}$, which can be the same or different than advertising duration $A_{dp}$. For ease of reference, advertising interval may be generally described as $A_i$ and advertising duration may be generally described as $A_d$, where the aforementioned $A_{ip}$, $A_{ir}$, $A_{dp}$, and $A_{dr}$, are examples of advertising intervals and durations associated with particular ones of display devices 120, discussed in greater detail below.

Figure 7B:
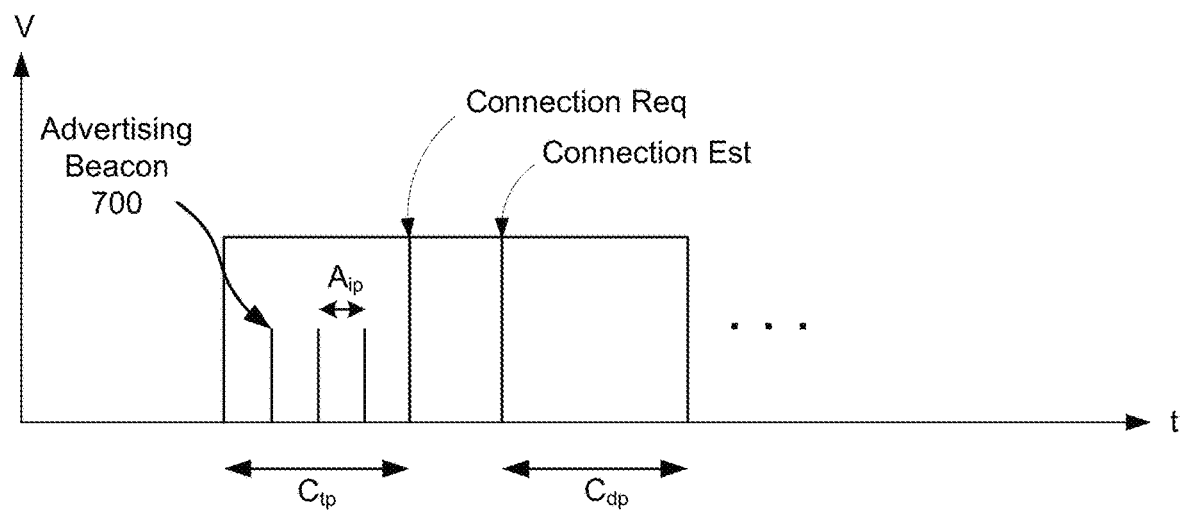
FIG. 7B is an example connection profile in accordance with various embodiments described in the present disclosure.

Advertising intervals, e.g., $A_{ip}$ or $A_{ir}$ and/or advertising durations, e.g., $A_{dp}$ or $A_{dr}$, may differ due to the type of display device/central to which radio 508 is advertising. In the above-described example, one display device, display device 120c, may be a handheld device, such as an iPhone®, which, due to its communication(s) characteristics stemming from the fact that it is a general purpose handheld device may necessitate a longer advertising duration $A_{dp}$ in order to receive an advertising beacon 700 and send a connection request back to radio 508. The CGM display device, i.e., display device 120a, being a dedicated receiver, may not need as long an advertising duration $A_{dr}$ because it is specifically configured to communicate with radio 508 of analyte sensor system 104. As alluded to above and discussed in greater detail below, advertising interval, e.g., $A_{ip}$ or $A_{ir}$ themselves may also differ based on the sensor information to be communicated to the display device, historical performance, etc. Additionally, and as discussed previously, different types of advertising can be achieved in accordance with various embodiments. For example, in whitelist advertising, only a targeted display device is allowed to engage in data exchange with sensor electronics module 106, where advertising beacons, such as advertising beacon 700 may include a specifically configured header or other identifier targeting a specific display device. Referring to FIG. 7B, if the connection request comes from the targeted display device, establishment of the connection can proceed. However, if the connection request comes from an un-targeted display device, connection establishment will not occur. As to directed advertising, a user may use an NFC-enabled display device 120c to, e.g., wake up sensor electronics module 106, which in turn may advertise to a particular display device, e.g., display device 120a, with advertising beacons targeted to display device 120, i.e., advertising beacon 702 having an advertising interval, $A_{ir}$, and advertising duration, $A_{dr}$. In one example, in addition to waking up the sensor electronics module 106, during the NFC based communication, the targeted display device may provide an advertising request to the sensor electronics module 106. In addition, the display device may, in some examples, may provide preferred advertisement intervals and advertisement durations parameters to the sensor electronics module. The electronics module 106 may then advertise to the targeted display device according to the provided parameters.

It should be noted that display devices contemplated by the present disclosure need not be limited to mobile communication devices, such as smart phones, and dedicated receivers, but can include any type of receiver appropriate for receiving sensor information in one or more forms/formats. For example, another type of display device/central may be a smart watch, e.g., display device 120b. In accordance with various embodiments, sensor electronics module 106 can categorize display devices based on their ability to scan, connect, and/or act as a proxy. That is, display device 120a, an example of a dedicated receiver in one embodiment, can connect only to analyte sensor system 104 via sensor electronics module 106, and may also scan for transmission packets (e.g., advertising beacons 700, 702 or EGV values) from radio 508 if a communication link is lost or dropped. Display device 120c may connect to analyte sensor system 104 via sensor electronics module 106, but may also connect to other devices, e.g., a WiFi access point, a mobile communications network, etc. Additionally, a handheld device, such as display device 120c, like a customized display device, i.e., display device 120a, may scan for transmission packets and may also act as a proxy for sending sensor data such as EGV data to a scan display. A display device, such as the aforementioned smart watch, i.e., display device 120b, may be categorized as being a "scan only" device, capable only of scanning for transmission packets with regard to analyte sensor system 104 if an existing connection is lost or dropped. That is, a scan only device cannot wirelessly connect directly to radio 508. As will be discussed in greater detail below, the capabilities of such display devices may change in other embodiments.

FIG. 7B illustrates an advertising and connection sequence or profile such as that illustrated in FIG. 4 in accordance with one example. Similar to the example illustrated in FIG. 7A, radio 508 may be in low power mode when CGM processor 506 is woken up via a wake event from wake source 502. CGM processor 506 may then obtain raw sensor data 504 from AFE 500, apply one or more algorithms to create/calculate an EGV value, and store that EGV value in memory, e.g., a flash database. At this point, advertising can begin and CGM processor 506 can signal radio 508 to start advertising (e.g., 3 seconds after the wake event). Radio 508 may advertise to, e.g., display device 120c, by sending advertising beacons/packets 700 in accordance with advertising interval $A_{ip}$. Although the predetermined advertising duration $A_{dp}$ for display device 120c may be 7 seconds, in this example, display device 120c to which advertising beacons 700 are targeted sends a command (connection) request sooner, reflecting a certain time-til-connection value, $C_{tp}$. Time-til-connection value, $C_{tp}$ is an example of a time-til-connection value, $C_t$, associated with the time it takes for a display device, in this case, display device 120c, to transmit a connection request to radio 508 in response to an advertising beacon broadcast by radio 508. Thereafter, a wireless connection is established between display device 120c and radio 508. A connection duration, generally described as $C_d$, can refer to the time period during which a display device is connected/in communication with radio 508. In this example, time period $C_{dp}$ specifies a connection duration for display device 120c. Once the requested commands have been processed, radio 508 may resume advertising, e.g., to another display device (advertising beacons 702). As will also be discussed below, varying connection duration and/or varying advertising and connection parameters based upon time-til-connection values can help extend battery life in accordance with various embodiments.

Figure 7C:
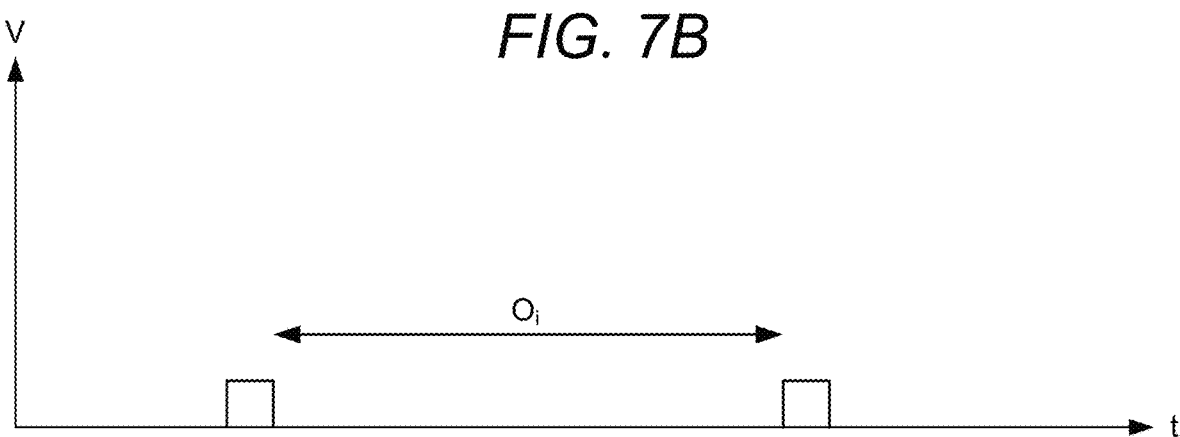
FIG. 7C is an illustration of an example operating interval in accordance with various embodiments described in the present disclosure.

FIG. 7C illustrates an example operating interval/frequency of transmission, $O_i$, which is indicative of time between when radio 508 is in low power mode/sleeping and when radio 508 wakes up and begins to advertise (as illustrated in FIG. 6). For example, if display device 120a has an active RF communication link, both the CGM application and radio application are in low power mode. The radio stack keeps the RF communication link open, and only when a command request is sent from display device 120a, will the radio/CGM applications exit low power mode.

Adjustable Variables

A plurality of options exist for varying or adjusting aspects of the advertising and connection protocol to minimize processing tasks, conserve battery power, improve connection reliability, etc. In accordance with some embodiments, one or more of the aforementioned communication aspects of the advertising and connection protocol can be treated as an adjustable variable.

—Transmission Variables

Examples of communication variables include those aspects of the advertising and connection protocol relevant to the manner in which data is transmitted, e.g., transmission frequency or operating interval (e.g., $T_{active}$ of FIG. 4, $O_i$ of FIG. 7, etc.), the transmission protocol utilized (Bluetooth, WiFI, NFC, ANT+, Zigbee, etc.), whether communications are one-way or two-way, and whether data is transmitted on-demand or whether the transmission of data occurs automatically. For example, it may be desirable to optimize communications based on the desired transmission protocol and/or transmission type to avoid wasting radio resources and/or battery life. In accordance with one embodiment, communication variables are adjusted to meet the desired transmission protocol and/or transmission type. In particular, and if, for example, the desired communication type is one-way communication, e.g., transmitting EGV data embedded in advertising beacons 700 and 702 from sensor electronics module 106 to display devices 120a and 120c, CGM processor 506 and radio 508 can be instructed/configured to operate such that no time is "set aside" for a connection duration $C_d$, i.e., $C_d=0$. Alternatively, CGM processor 506 and radio 508 can be instructed/configured to operate without any connection duration, $C_d$.

—Advertising Variables

Other examples of communication variables include aspects of the advertising and connection protocol, and may include the following: how a data packet is formatted, e.g., the advertising beacon packet may include sensor data rather than merely radio identification information, scan device data, etc.; the manner in which a data packet is encrypted; the advertising duration $A_{dx}$; the advertising interval $A_{ix}$; and the power used when broadcasting advertisements (e.g., dBm of radio 508).

Referring to the above example, and as illustrated in the example of FIG. 7A, the advertising durations, e.g., $A_{dp}$, $A_{dr}$, can abut each other if communications are one-way. Again, this may be the case if EGV measurements or EGV trend information is included in one or more advertising beacons 700, 702 and connections to display devices 120a and 120c are not warranted/needed. Moreover, the advertising duration $A_d$ and advertising interval $A_i$ may be decreased because radio 508 is not expecting to establish an actual wireless communication session with display devices 120a and 120c. Operating interval $O_i$ can commensurately be increased. In some embodiments, the configuring of advertising durations, $A_d$, may be ignored or bypassed altogether.

Still other examples of communication variables include the type of the display device (e.g., general purpose handheld device such as display device 120c, dedicated receiver such as display device 120a, diagnostic device, consumer device, etc.); the number of display devices available to connect to the analyte sensor system 104; the order in which the display devices 120 connect to the analyte sensor system 104; how and/or whether or not a display device is determined to be a primary display device; and the broadcast mode commensurate with the role (primary or peripheral) of the display device.

As can be appreciated, and as alluded to previously, advertising intervals $A_i$ and advertising durations $A_d$ may be varied according to the type of display device for which the advertising beacons are intended. For example, display device 120a, a dedicated CGM display device, may have a shorter advertising duration $A_{dr}$ than that of display device 120c, a handheld device, e.g., mobile phone. In accordance with another example, in a scenario where only a single display device, e.g., display device 120c, has been able to connect to radio 508, its respective advertising duration $A_{dp}$ may be increased in order to ensure that sensor information is transmitted and observable by a user. In the event that more than one of the display devices 120 have established previous wireless connection sessions with radio 508 (e.g., by accessing and reviewing the bonding list), respective advertising durations $A_d$ may be shortened under the assumption that establishing a wireless connection session between sensor analyte system 104 and any particular one of display devices 120 is less critical.

Conditions for Adjusting Variables

As discussed above, certain communication variables can be adjusted to affect battery usage and improve connection reliability. The manner in which those communication variables can be adjusted may be dependent upon one or more conditions for communication described in greater detail below that include, but are not limited to display devices populating the whitelist and/or bonding list that can be indicative of historical and/or predictive connections, as well as the condition of the user/host 102.

—Whitelist, Current and Historical Communications/Connections, and Time

Examples of communication conditions upon which adjusting the above-described communication variables are based can include conditions having to do with which display device(s) populate the whitelist and/or which display device is currently connected or unconnected. Returning to the above example, the existence of multiple display devices 120 to connect to, which can result in a decrease in respective advertising durations $A_d$ may be based upon multiple display devices 120 populating the whitelist, while an advertising duration $A_d$ may be increased in the event that only one corresponding display device, e.g., display device 120a, populates the whitelist.

Another example of communication conditions can include historical or previous communications such as the following: the number of previously missed communications; a previous advertising interval/duration "budget;" and historical time-til-connection associated with a particular display device. That is, CGM processor 506 may remove a display device populating the whitelist in the event that a predetermined threshold amount of time during which the display device has failed to connect with sensor electronics module 106 has been exceeded. Still other examples of communication conditions may include, e.g., the time of the last communication with one or more display devices and/or a current time of day or date. That is, if the number of previously missed communications, i.e., advertising beacons, such as advertising beacons 700 for display device 120*c* go unanswered for some predetermined time threshold, the advertising duration $A_{dr}$ for display device 120*c* may be reduced or eventually set to 0. This may be the case, for example, if a user returns to his/her home and turns his/her mobile phone off or stores it in some location not reachable by the currently implemented wireless communication protocol. Similarly and regarding previous advertising interval/duration budget, the CGM processor 506 may have radio 508 advertise to one or more of display devices 102 in accordance with a previous advertising interval, A, and duration, $A_d$ unless missed communications and/or historical time-til-connection statistics indicate to the CGM processor 506 that the advertising interval, A, and duration, $A_d$ should be adjusted to comport with current communication conditions. For example, CGM processor 506 can review historical time-til connection $C_{tp}$ values associated with display device 120*c*. If the time-til connection $C_{tp}$ values are short (e.g., in the event that the user is at work and may consistently have his/her phone in his/her possession), CGM processor 506 can advertise to display device 120*c* in accordance with a shortened advertising duration $A_{dp}$. In other words, communication conditions in which a display device connects sooner than expected can be interpreted by CGM processor 506 to indicate that connection reliability is sufficiently good and that the current advertising interval/duration budget may be too generous thereby resulting in an unnecessary expenditure of battery power.

—Sensor Data and User/Sensor Condition

In accordance with some embodiments, communication conditions upon which adjusting communication variables are based may include a user condition. For example, depending on one or more of actual and/or predicted sensor or EGV data or sensor or EGV data trends can affect one or more communication variables. The same may be true of alarm or alert conditions, e.g., low, high, trending, or boundary alarms. The condition of sensor analyte system 104 itself, such as whether or not sensor calibration of continuous analyte sensor 108 is required, completed, or results in error, or whether continuous analyte sensor 108 is nearing or at the end of its useful life can affect one or more communication variables. Temperature of host 102 is also another communication condition, as is sensed physical movement. Additionally, signal noise is yet another communication condition that may be measured and relied upon as a basis for adjusting one or more communication variables.

Figure 8A:
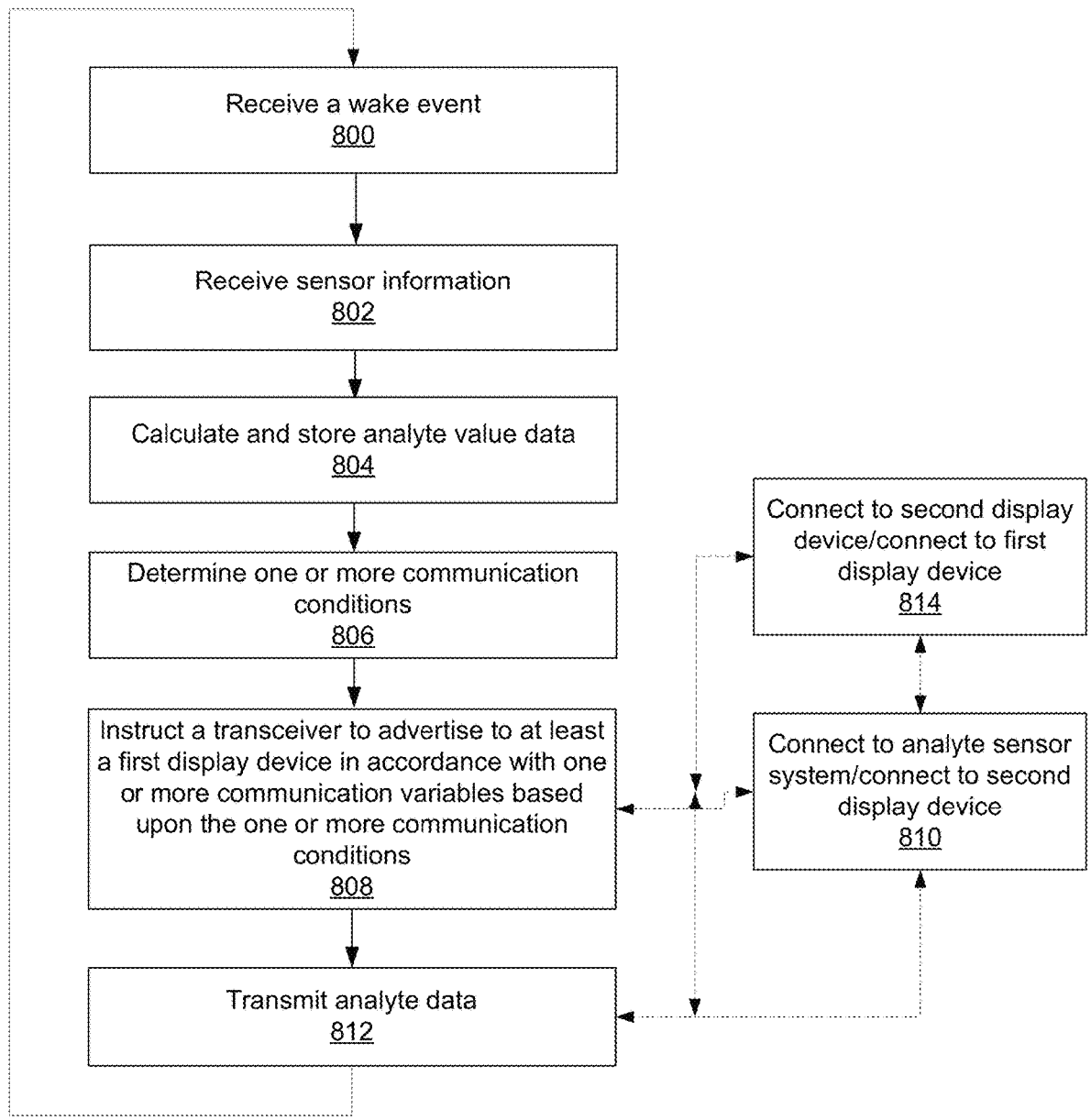
FIGS. 8A-8H are flow charts illustrating example processes performed for adapting communications in accordance with communication conditions and communication variables in accordance with various embodiments of the present disclosure.

FIG. 8A is a flow chart illustrating example processes performed for advertising, connecting to, and communicating analyte data in accordance with various embodiments. At operation 800, a wake event is received, e.g., by a CGM processor 506 of the analyte sensor system 104. At operation 802, sensor information is received by the CGM processor 506. At operation 804, analyte data, e.g., EGV data, is calculated and stored by the CGM processor 506. For example, the sensor information received by CGM processor 506 may be raw sensor data, which can then be processed to arrive at the analyte value data. In some embodiments, the sensor information, e.g., raw sensor data, can be passed to CGM processor 506 directly. At operation 806, one or more communication conditions is determined as described above. That is, conditions that may have an effect on the advertising to one or more of display devices 120 and/or resulting wireless communication sessions established between the one or more display devices 120 and CGM processor 506 can be considered for adjusting or optimizing communication variables. At operation 808, a transceiver, e.g., radio 508, is instructed to advertise to at least a first display device, e.g., display device 120*c*, in accordance with one or more communication variables (e.g., $A_{ip}$, $A_{dp}$, $C_{tp}$) based upon the one or more communication conditions. At operation 810, the first display device, display device 120*c*, may connect to the transceiver, radio 508, of analyte sensor system 104. At operation 812, analyte data is transmitted to the first display device, display device 120*c*. It should be noted that as will be discussed below, a myriad of different/alternative advertising and/or communication schemes can be used. Accordingly, at operation 814, the transceiver, radio 508 of the analyte sensor system 104 may connect to and/or transmit analyte value data to a second display device, e.g., display device 120*a*. As will also be discussed below, the first and second display devices may connect to each other in addition to or as an alternative to connecting to the analyte sensor system 104.

Figure 8B:
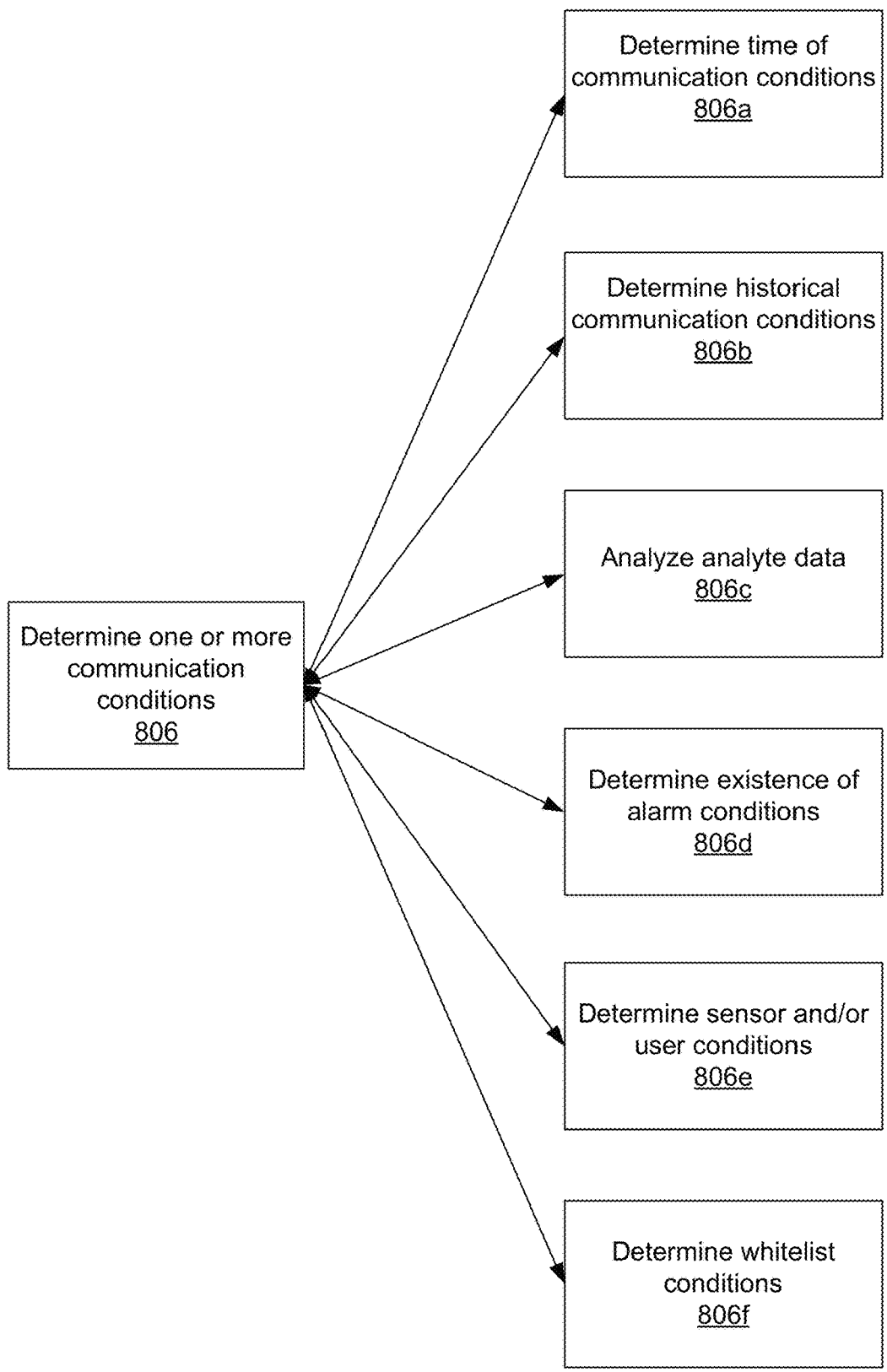
Figure 8C:
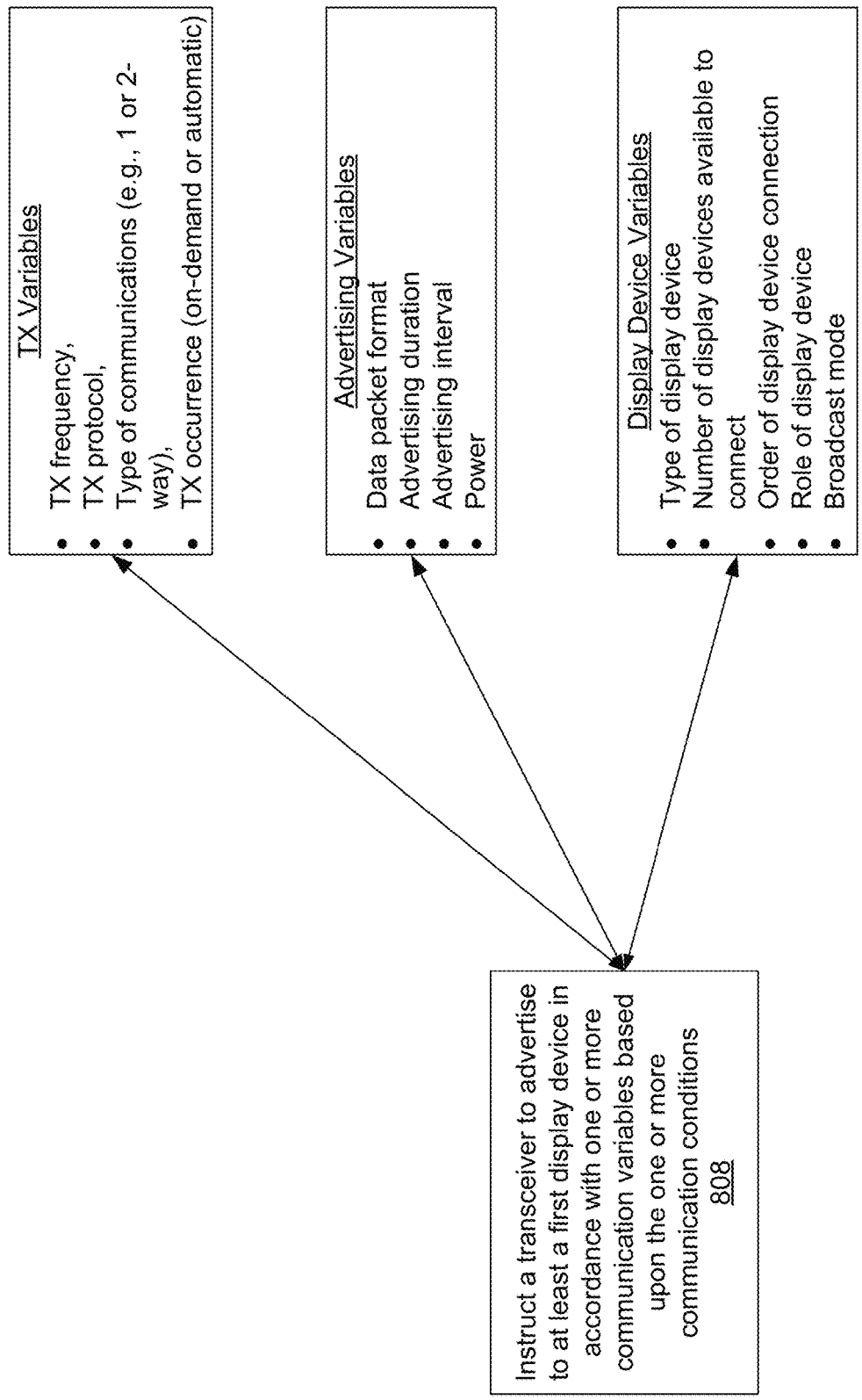

FIG. 8B illustrates a plurality of communication conditions 806*a*-806*f* (discussed previously) that may be determined or measured in accordance with operation 806 of FIG. 8A. FIG. 8C illustrates a plurality of advertising, communication, and display device-based variables that can be adjusted in accordance with operation 808 of FIG. 8A.

Intelligent Advertising

As previously discussed, various embodiments contemplate adjusting one or more variables based on one or more communication conditions in order to optimize the advertising and connection process such that advertising and connections can be achieved with sufficient reliability to provide meaningful sensor data while extending battery power. In other words, various embodiments achieve a balance between battery power and connection reliability. For example, and in the context of advertising, advertising variables can be set or selected based on some minimum reliability to avoid or lessen the occurrence of missed advertising beacons when the advertising interval is short (to avoid excessive battery drain on radio 508 as a result of longer advertising intervals).

In some embodiments, the order of display devices 120 and/or which of display devices 120 connect to sensor electronics module 106 can impact battery power and/or connection reliability. Accordingly, whitelist conditions can be determined. That is, CGM processor 508 can access the whitelist to determine which display device(s) 120 are currently present within the whitelist. For example, CGM processor 508 may adjust the advertising interval/duration budget to include only the requisite advertising interval/duration for display devices present in the whitelist so that, as previously described, battery power and radio resources are not wasted, e.g., by advertising to display devices that have a low likelihood of connecting. Thus, advertising beacons are not sent to display devices not currently included in the whitelist. Moreover, advertising to only those display devices present in the whitelist can result in the ability to provide, e.g., a greater advertising duration for those display devices, thereby increasing connection reliability. That is, if an advertising duration has an X-second budget for advertising to display device 120c (e.g., $X_p$ seconds) and display device 120a (e.g., $X_r$ seconds), but display device 120a is not present in the whitelist, the radio 508 can be instructed to allocate an additional $X_r$ seconds (or some amount of time based on $X_r$ seconds) when advertising to display device 120c, or to advertise to another display device 120b, d, or e.

As alluded to previously, NFC-capable display devices may alter the "normal" establishment of communications. For example, a user may wish to have analyte sensor system 104 transmit sensor information prior to a scheduled transmission. This can be due to the user/host 102 feeling the onset of a hypoglycemic condition, or the user may wish to have a backlog of sensor data transmitted in a "data dump" to one of display devices 120. In operation, a user can invoke directed advertising through the use of NFC-capable display device, e.g., display device 120c. As previously discussed, directed advertising allows a display device, e.g., display device 120c to "tap" display device 120c on analyte sensor system 104 (e.g., bringing the display device substantially close to the analyst sensor system to effectuate an NFC communication) thereby instructing CGM processor 506 to wake up (where sensor electronics module 106 may have a separate NFC transceiver (not shown)). CGM processor 506 may then instruct radio 508 to begin advertising to display device 120c or to another one of display devices, e.g., in accordance with an advertising order based on the whitelist, for example, a most recent connection, or some other preferred display device. CGM processor 506 may also access historical EGV data (discussed further below) and determine that the user/host 102 is trending towards a potential hypoglycemic condition in which case, CGM processor 506 may attempt to establish a wireless connection with display device 120a and may further increase the advertising duration $A_{dr}$ in order to increase the chances of establishing a wireless communication session. Alternatively still, upon the user invoking directed advertising, analyte sensor system 104 may access the whitelist to determine which of display devices 120 populates the initial position, which in some embodiments can indicate the "preferred" or "primary" display device. Analyte sensor system 104 would then attempt to establish a wireless communication session with that preferred/primary display device.

It may be beneficial to have display devices optimal for a particular scenario present/populating the whitelist so that a wireless communication session can be established quickly. Thus, in accordance with some embodiments the whitelist is updated in accordance with condition of the whitelist itself. That is, the presence of certain display devices having certain capabilities can be used to initiate, e.g., the removal of other display devices not compliant with those capabilities. For example, the existence of an NFC-capable device, e.g., display device 120c, in the whitelist may prompt the removal of a non-NFC-capable display device, e.g., display device 120d because a user may rely on the NFC capabilities of display device 120c to obtain EGV data, or alternatively, to pair/initiate the wireless communication session, thereby disqualifying display device 120d.

Figure 8D:
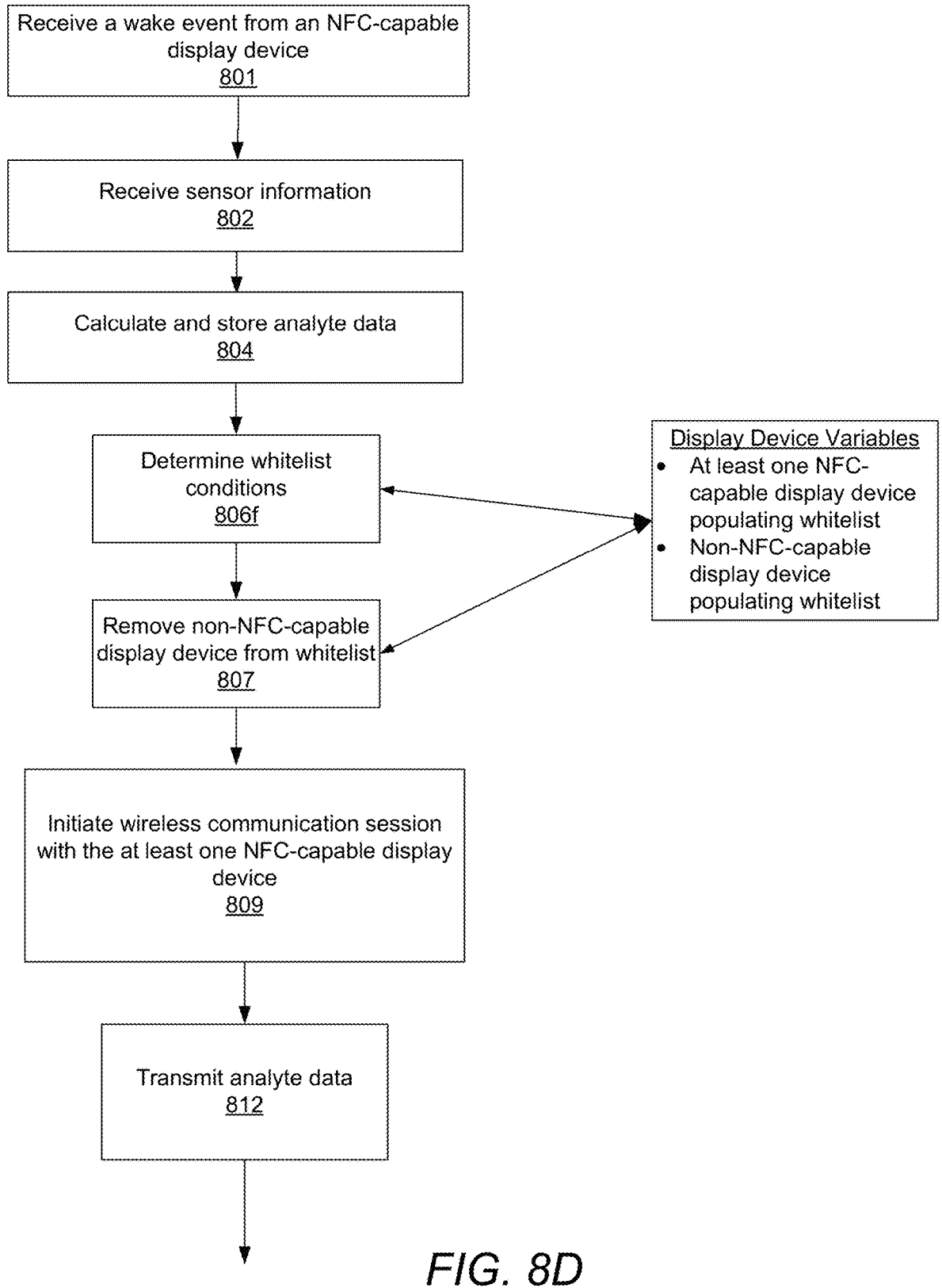

FIG. 8D illustrates example processes performed for updating the whitelist in accordance with this embodiment. At operation 801, a wake event is received, the wake event being initiated by an NFC-capable device. That is, display device 120c, which may be a smart phone, can be tapped on analyte sensor system 104 to initiate a wake up signal to be sent from AFE 500 (FIG. 5) to CGM processor 506. Similar to FIG. 8A, CGM processor 506 can receive sensor information at operation 802, and analyte data is calculated and stored at operation 804. At operation 806f, whitelist conditions are determined. As described above, in this example, at least one NFC-capable device is populating the whitelist, e.g., display device 120c, along with a non-NFC-capable device, e.g., display device 120d. At operation 807, the non-NFC-capable display device is removed from the whitelist. At operation 809, a wireless communication session is initiated with the at least one NFC-capable display device. Thus, an NFC process can be used to effectuate the wireless communication session with display device 120c, or with another NFC-capable device, e.g., display device 120b. At operation 812, the analyte data is transmitted to one of display device 120c or display device 120b. In this way, time and resources need not be wasted advertising to display device 120d. It should be noted that although this embodiment is disclosed in the context of removing a non-NFC-capable device, other conditions and actions regarding device capabilities and whitelist updates, whether display devices are added, removed, re-ordered, etc. are contemplated. In some embodiments, display devices, for example, display device 120c may include both NFC and non-NFC communication protocol (e.g., a BLE communication protocol). As such, when it is determined that the display device 120c has NFC capability, device 120c may also be taken out of the whitelist, so that analyte sensor device 104 communicates analyte sensor data to the display device 120c only via NFC communication, rather than via BLE communication protocol.

As alluded to previously, adhering to set advertising and/or connection parameters may result in wasting radio resources as well as result in less reliable communications. In some embodiments, historical communication conditions can be determined or analyzed in order to optimize the advertising duration. For example, the advertising and connection software can be configured to operate using an algorithm that varies the advertising duration based upon historical statistics or information regarding time-til-connection periods. That is, the CGM processor 506 can instruct the radio 508 to progressively lessen the advertising duration by some predetermined amount until a measured connection rate for one or more display devices drops below a predetermined connection rate or percentage threshold. Alternatively, the advertising duration can be progressively decreased depending the lack of a connection, e.g., if a display device, e.g., display device 120c (having an advertising duration $A_{dp}$ of $X_p$ seconds) has not connected to the analyte sensor system 104 within the last 5 minutes, the advertising duration $A_{dp}$ for display device 120c will be reduced to $X_p'$ seconds from $X_p$ seconds, and so on. The lack of connection may suggest the absence of display device 120c, and battery power can be conserved by stepping down the advertising duration $A_{dp}$ or eventually stopping the transmission of advertising beacons 700 altogether, and, e.g., advertising to another display device. If, however, display device 120c comes back into range of analyte sensor system 104, e.g., prior to the end of the transmission of advertising beacons 700, or if the user initiates directed advertising to display device 120c, the algorithm can reinstate the advertising duration $A_{dp}$ for display device 120c (either in full, e.g., $X_p$ seconds, or in a progressively increasing manner based upon additional, subsequent wireless communication sessions being established).

The algorithm may alternatively or additionally predictively estimate what display devices are likely to be within range of the analyte sensor system, and tailor the advertising duration(s) to those display devices. In particular, the algorithm may instruct CGM processor 506 to access memory 318, for example, to analyze historical connection statistics. Based on the historical connection statistics, the algorithm may generate an advertising profile that optimizes the likelihood of connection to one or more display devices 120. Historical connection statistics can include, e.g., the times of day that a particular display device connects to analyte sensor system 104. Historical connection statistics can also include, as previously discussed, previous advertising interval/duration budgets as well as historical time-til-connection durations, $C_d$.

For example, based on the historical connection statistics, it may be determined that from the hours of 6 pm to 6 am, display device 120c does not usually respond to advertising beacons 700, whereas display device 120a does. Accordingly, radio 508 can be instructed to only advertise (using advertising beacons 702) to display device 120a from the hours of 6 pm to 6 am using the appropriate advertising duration $A_{dr}$ for display device 120a. As another example, the algorithm may determine the number of recent connections that occur for particular display devices, the amount of missed advertising packets associated with particular display devices, etc. and instruct radio 508 to advertise to those display devices (using the appropriate advertising duration) having successfully connected during some recent time period, and to skip advertising to those display devices associated with missed advertising packets.

Still other embodiments may operate based on an analysis of EGV and/or raw sensor data. For example, the CGM processor 506 may alter advertising duration and/or advertising intervals for one or more display devices according to a user's state based on the EGV and/or raw sensor data. That is, if EGV data indicates that the user is going hypoglycemic, the advertising duration for one or more display devices can be increased and/or the advertising interval can be shortened in order to reduce the chance that advertising beacons will be missed. Yet, during non-critical periods, e.g., when the EGV data indicates that the user is in a healthy state, the same advertising duration can be shortened and/or the same advertising interval can be increased, as providing the EGV data is less critical. Thus, the establishment of a wireless communication session can be delayed.

Figure 8E:
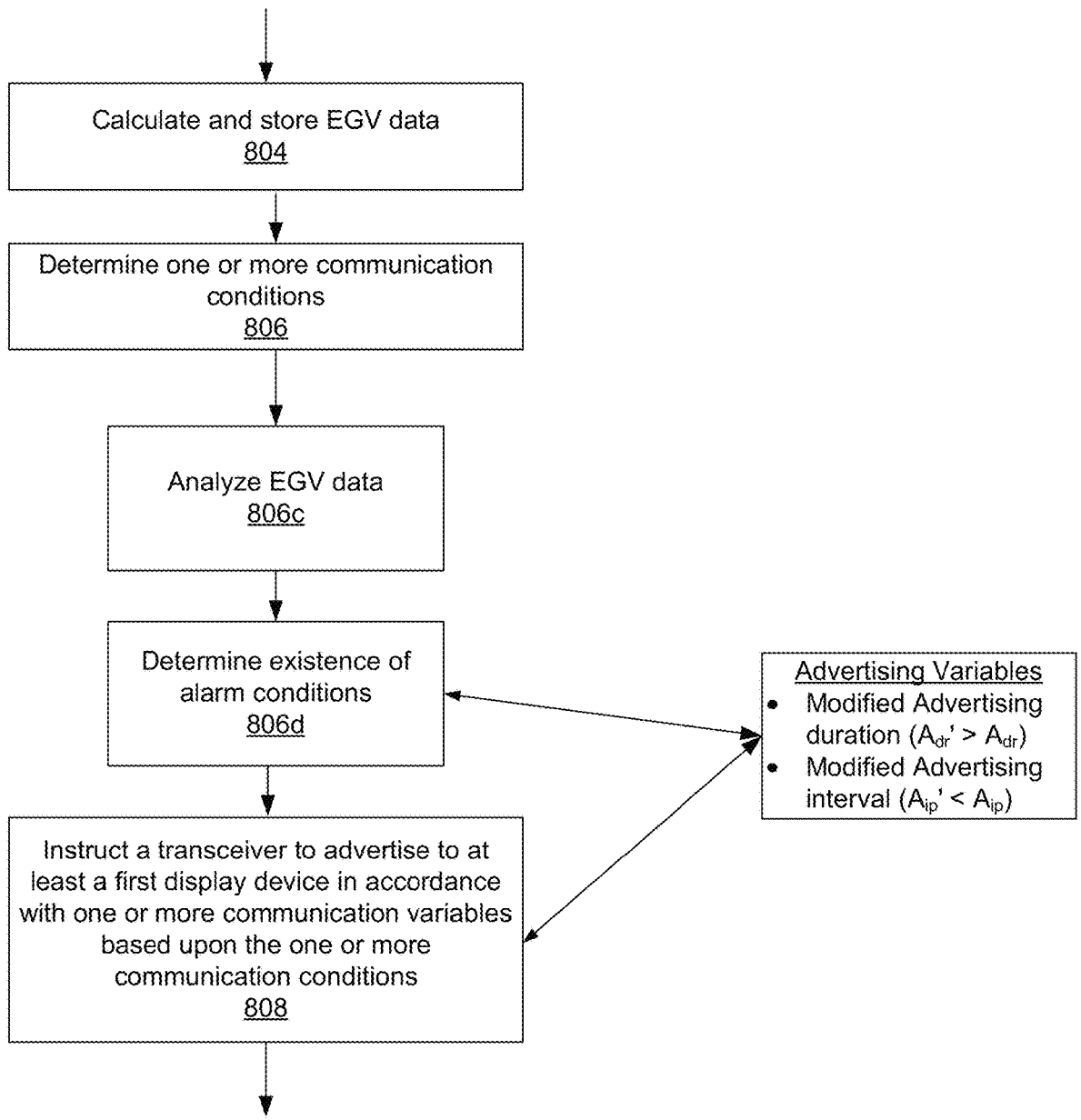

FIG. 8E is a flow chart illustrating example processes performed in accordance with the above example scenario, and will be described with reference to previously described FIGS. 1, 6, and 7 for ease of understanding.

CGM processor 506 may calculate analyte data and store that calculated analyte data (operation 804 and process 604 of FIG. 6). It should be understood that operations 800 and 802 (illustrated in FIG. 8A) may have already been performed, i.e., a wake event may have already been received, and CGM processor 506 may have already received sensor information from analyte sensor system 104, thereby allowing CGM processor 506 to calculate the analyte data. In accordance with one or more algorithms utilized in controlling CGM processor 506, CGM processor 506 may be instructed to determine one or more communication conditions (operation 806). In this example, CGM processor 506 may be instructed to analyte EGV data (operation 806c) which includes historical EGV data. Thus, CMG processor 506 may access its database and review some predetermined number of (or for some predetermined amount of time) calculated EGV values to determine a recent trend of analyte (in this case, glucose) measurements. If the observed trend of analyte measurements indicates that the user (e.g., host 102 of FIG. 1) may be falling into a hypoglycemic condition, CGM processor 506 can determine the existence of an alarm condition (operation 806d). As such, CGM processor 506 can start advertising (operation 808 and process 606 of FIG. 6) sooner than may be "normally" configured with radio 508, prompting radio 508 to begin advertising to one or more display devices 120. Moreover, the advertising interval $A_{ip}$ (FIG. 7) for one or more of display devices 120, e.g., display device 120c, may be shortened, resulting in more frequent advertising beacons 702 being transmitted in an attempt to increase the chance of connection. Alternatively or in addition, the advertising duration $A_{dr}$ can be increased for display device 120a. For example, given that display 120a, a dedicated CGM display device, may have the greatest chance for connection to radio 508 of sensor electronics module 106, the advertising duration $A_{dr}$ can be increased for that specific display device. It should be noted that the requisite connections/wireless communications sessions/transfer of EGV data can occur as illustrated in FIG. 8A.

Returning to FIG. 7, it can be appreciated that the advertising duration, $A_d$, can be altered depending on the transmission protocol currently being/to be utilized. That is, certain transmission protocols may have a smaller "operative distance" between peripheral and central(s). For example, when utilizing NFC, CGM processor 506 can generate/calculate advertising durations for one or more of display devices 120 that have been shortened based on the assumption that the one or more display devices 120 will be close to analyte sensor system 104 and will not likely require extended advertising durations. Additionally, the advertising durations of non-NFC display devices may be negated when the wireless communication session initiation/pairing is accomplished using NFC.

In other embodiments, a user's temperature and/or predicted or determined activity level or lack thereof can be used as a condition upon which advertising is based. For example, analyte sensor system 104 may employ one or more accelerometers or other sensors capable of determining the activity level of a user/host 102. Upon CGM processor 506 determining, based on feedback from analyte sensor system 104 that a user is assumed to be sleeping, e.g., based on sensed lack of movement or time of day, advertising durations $A_d$ for one or more display devices 120 may be reduced unless a critical or alarm condition is sensed. Alternatively, CGM processor 506 may determine, based on feedback from analyte sensor system 104 that a user/host 102 is assumed to be engaged in some activity, e.g., running. In this case, CGM processor 506 can instruct radio 508 to advertise only to a display device that the user is likely to have on his/her person, such as a smart watch, i.e., display device 120b, rather than another display device, such as a tablet PC, i.e., display device 120d. The determination regarding which display device(s) the user is likely to have on his/her person can be made based on which display device(s) are populating the whitelist, one or more display device type identifiers, historical information, time of day information, etc. (discussed previously).

It should be noted that the existence or absence of alerts/alarm conditions or triggers, approaching an alert/alarm condition, EGV/raw sensor trending data or predictions can be leveraged in the same manner. For example, EGV or raw sensor data can be analyzed by CGM processor 506 to determine whether a user is trending towards, e.g., a hypoglycemic condition, and/or predictive algorithms can be used to predict a user's current or future state, and advertising duration $A_d$ and/or advertising interval $A_d$ variables can be adjusted commensurate with that data/prediction(s). It should also be noted that the amount of power used for transmitting each advertising beacon can be adjusted based on the same or similar communication conditions used to adjust the advertising duration and/or interval. For example, if display device 120*b*, i.e., a smart watch, connects to analyte sensor system 104, CGM processor 506 may instruct radio 508 to reduce the power used to transmit advertising beacons inasmuch as it may be assumed that display device 120*b* will be on the user's body/wrist, near sensor electronics module 106. Thus, less power is likely needed for the advertisement beacons. It should be noted that the transmission power for communicating sensor information/analyte data may also be decreased.

Relying solely on the sensor electronics module 106 of analyte sensor system 104 to effectuate data transfer to one or more of display devices 120 can be taxing from a battery power perspective. In accordance with other embodiments, networking techniques or architectures can be leveraged, e.g., mesh networking, to reduce advertising as well as connection frequency. For example, a first display device, e.g., display device 120*c*, may connect to analyte sensor system 104. Thereafter, display device 120*c* may advertise to one or more additional devices, e.g., display devices 120*b* and 120*d*, so analyte sensor system 104 need not have to deplete its own battery power to transmit advertising beacons, connect to other display devices, etc. Moreover, depending on the type of display devices present, analyte sensor system 104 may not be an optimal connection/communication candidate. Accordingly, and again, networking or "direct" communications between display devices may result in better connection reliability. For example, display devices 120*b* and 120*c* may be optimized for data transfer therebetween, such that data communications between display devices 120*b* and 120*c* are more reliable than between, e.g., display device 120*b* and analyte sensor system 104.

In some scenarios, it may be beneficial to allow a user to control which display device(s) 120 connect to analyte sensor system 104 to receive sensor data. Thus, in accordance with some embodiments, the whitelist can be user-modifiable or updatable. In particular, a user may specify a desired display device to connect to by accessing the whitelist which can be stored, e.g., in memory 318, and interacting with the whitelist through a user interface provided on one or more of display devices 120. In this way, radio 508 need not transmit advertising beacons to a display device that the user does not intend to rely on. As described previously, a whitelist may be a list of display devices reflecting those display devices that have successfully been paired or bonded with the sensor electronics module 106.

Figure 8F:
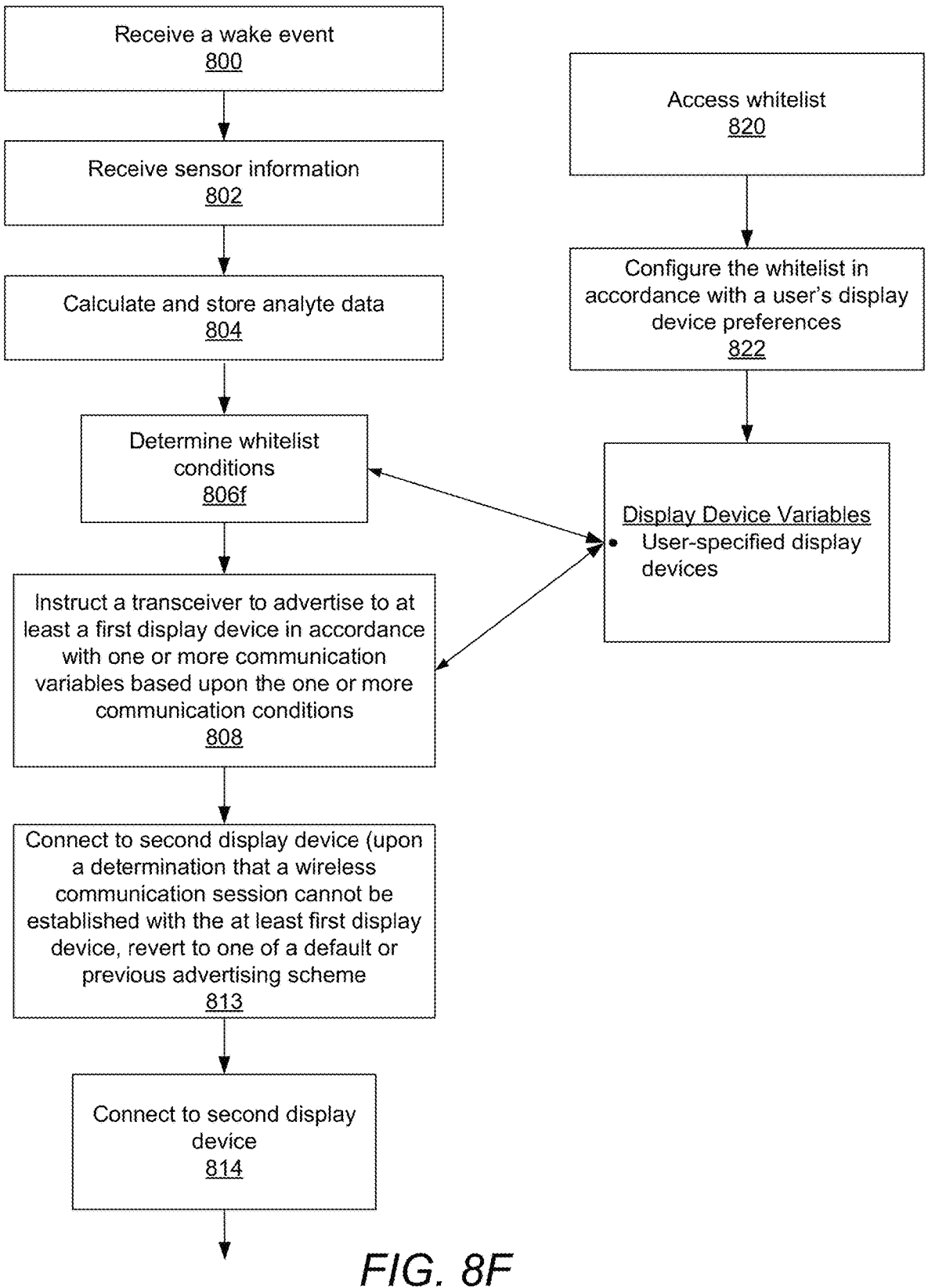

FIG. 8F is a flow chart illustrating example processes performed in accordance with the above-described scenario. Like FIG. 8A, a wake event is received at operation 800, sensor information is received, e.g., by CGM processor 506, at operation 802, and at operation 804, analyte data can be calculated and stored by CGM processor 506 based on the received sensor information. At operation 806, whitelist conditions are determined, one aspect of communication conditions, as discussed above. As alluded to above, the whitelist can be configured/updated by the user either directly or indirectly (e.g., via manipulation of another display device list that is different than the whitelist). Thus, at operation 820, the whitelist is accessed, e.g., by CGM processor 506 vis-à-vis an instruction by a user interface providing user control over the whitelist. At operation 822, the whitelist is configured in accordance with the user's display device preferences. Returning to operation 808, a transceiver, e.g., radio 508, can be instructed by CGM processor 506 to advertise to at least a first display device in accordance with one or more communication variables based upon the one or more communication conditions. In this instance, the advertising is performed based on the whitelist configured/updated by the user. If that specified display device does not connect, the radio 508 can be instructed to return to a default or previous advertising scheme (with the appropriate advertising duration/time/power) at operation 813. For example, the user may specify that display device 120*b* is to be used for the establishment of a wireless communication session and transfer of EGV data from some period of time. This may occur, for example, if the user is exercising and wishes to receive sensor information on a convenient display device, in this case, display device 120*b*, a smart watch. However, if the user forgets to wear display device 120*b*, after some threshold time of failing to establish a wireless communication session with display device 120*b*, radio 508 can be instructed to begin transmitting advertising beacons in accordance with a default whitelist population. At operation 814, connection to a second display device is established (based upon the default or previous advertising scheme).

In still other embodiments, the order in which display devices connect to the analyte sensor system 104 may also be leveraged to save battery power as well as increase connection speed and connection reliability. For example, if EGV data suggests that a user is nearing a hypoglycemic state, radio 508 may transmit advertising beacons 702 to a last connected display device or a default display device, such as display device 120*a*, a dedicated CGM display device, so that the likelihood of connection is heightened while also potentially reducing wasted battery power by advertising to a display device that is unlikely to connect. Moreover, advertising can be adapted such that advertisement beacons are only sent to a particular display device depending on which display device(s) has/has not connected, e.g., advertisements to display device 120*b* associated with a display device 120*c* may be transmitted only if display device 120*c* is/has connected to radio 508.

In accordance with another embodiment, the whitelist may be used to force a connection with a preferred display device, e.g., display device 120*b* (in the previously described example) and then the aforementioned mesh networking scheme can be leveraged such that the preferred display device, once connected, can assume the role of advertising to additional display devices. That is, and in this instance, display device 120*b*, may connect to analyte sensor system 104. Thereafter, display device 120*b* may advertise to one or more additional devices, e.g., display devices 120*a* and *d*, so analyte sensor system 104 need not have to deplete its own battery power to transmit advertising beacons, connect to other display devices, etc.

Figure 8G:
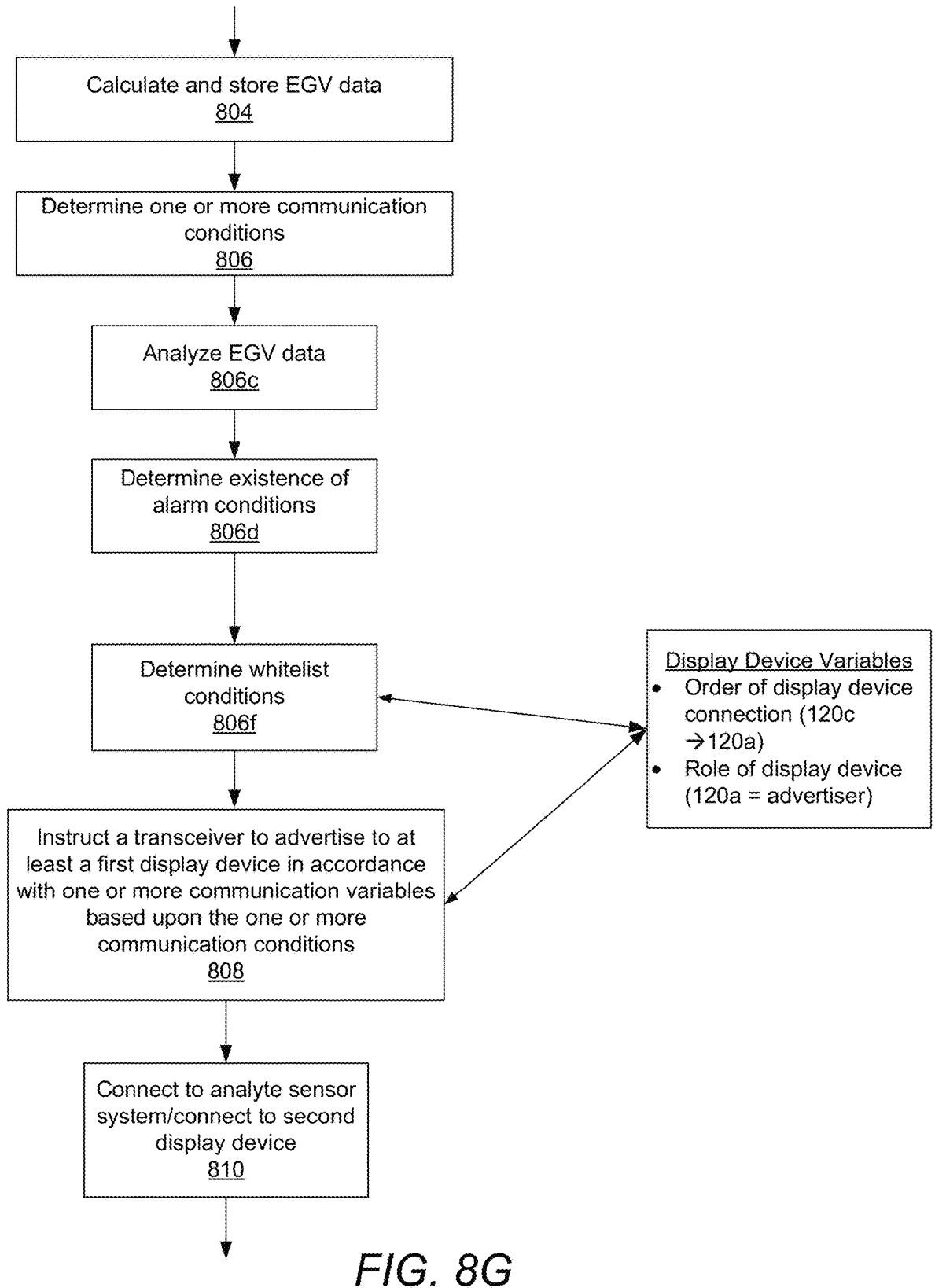

FIG. 8G is a flow chart illustrating example processes performed in accordance with the above example scenario, and will be described with reference to previously described FIGS. 1, 6, and 7 for ease of understanding. Like the flow chart of FIG. 8E, CGM processor 506 may calculate an EGV value and store that calculated EGV value (operation 804 and process 604 of FIG. 6). It should be understood that operations 800 and 802 (illustrated in FIG. 8A) may have already been performed. In accordance with one or more algorithms utilized in controlling CGM processor 506, CGM processor 506 may be instructed to determine one or more communication conditions (operation 806). In this example, CGM processor 506 may be instructed to analyte EGV data (operation 806*c*) which includes historical EGV data. Thus CMG processor 506 may access its database and review some predetermined number (or for some predetermined amount of time) calculated EGV values to determine a recent trend of analyte (in this case, glucose) measurements. If the observed trend of analyte measurements indicates that the user (e.g., host 102 of FIG. 1) may be falling into a hypoglycemic condition, CGM processor 506 can determine the existence of an alarm condition (operation 806*d*). However, in this example, display device variables are taken into consideration, where the order of display device connection (determined via the whitelist conditions at operation 806*f*) may be the following: display device 120*c* connected first; display device 120*a* connected second. Thus, per the above scenario, radio 508 is instructed to transmit advertising beacons 702 (FIG. 7) to display device 120*a*, the last connected display device (operation 808). Display device 120*a* may then connect to analyte sensor system 104 (in particular, radio 508) and a wireless communication session can be established (operation 810). Moreover, the role of the display device may also be considered. In this scenario, display device 120*a* is configured to act as an advertising entity. Thus, display device 120*a* may continue with advertising to display device 120*c* and connect thereto (operation 810). EGV data my then be transmitted per operation 812 of FIG. 8A and so on.

Intelligent Communication

While intelligent advertising schemes or techniques can be utilized to conserve battery power, actual communications between analyte sensor system 104 and one or more display devices 120 can also be made more efficient to also reduce the drain on the sensor electronics module's battery.

To achieve efficient communications, some embodiments may adjust the frequency with which EGV data is transmitted (illustrated as, e.g., first data communication 416, second data communication 424, etc.), i.e., the update frequency. As described above, with regard to actual, trending, and/or predicted data, alerts/alert boundaries, as well as alarms/alarm conditions, the frequency with which data is sent can vary, i.e., less frequently when the user is in a clinically "safe" zone and more frequently when the user is in or is nearing a potentially clinically unsafe condition, e.g., a hypoglycemic state. In accordance with one embodiment, EGV data is only transmitted upon the satisfaction of an alert condition, thereby significantly reducing the battery power that would be conventionally consumed if such data were being sent more frequently.

A user may also be allowed to set the update frequency (discussed above) to conserve battery power. For example, the user may be allowed to specify that if a last EGV calculation is within some range (e.g., percentage) of a median bound, then a particular update frequency can be employed. Similar to updating the whitelist described above, a user interface may be provided in one or more display devices 120 (or directly on analyte sensor system 104, e.g., on sensor electronics module 106). The user interface can be accessed by the user, where the user interface provides a mechanism for indicating an EGV threshold that is used as a basis for update frequency. However, in the event of a recent calibration, a recent dose of insulin (e.g., from display device 120*e*, a medicament delivery device), or consumption of carbs, communications can be established immediately and/or the update frequency can be increased.

In order to increase battery life and/or connection reliability, it may be beneficial to allow transmission modes to be specified or controlled to comport with certain communication conditions. For example, two-way communications which require power to be supplied to, e.g., sensor electronics module during transmission and receipt of data, may be unnecessary in certain scenarios. Thus, a user's condition may be used as a basis for determining a mode of transmission. In particular, some embodiments may allow CGM processor 506 to base a mode of transmission on sensor or EGV data, where one-way or two-way communications can be effectuated depending on the data received/calculated by the CGM processor. For example, if a user's is not in a critical state, transmissions can occur using, e.g., a one-way burst transmission (as described above), but if the user enters or nears a critical state, the transmission mode may switch to two-way communications or other communication protocols, where the user can request EGV data on-demand (e.g., via NFC). Still other circumstances where a transmission mode can be adapted include times when analyte sensor system 104 is undergoing calibration. As another example, a transmission mode can be adjusted in response to a situation where a wireless communications session cannot be established over one or more update periods resulting in missed sensor information that should be backfilled.

Figure 8H:
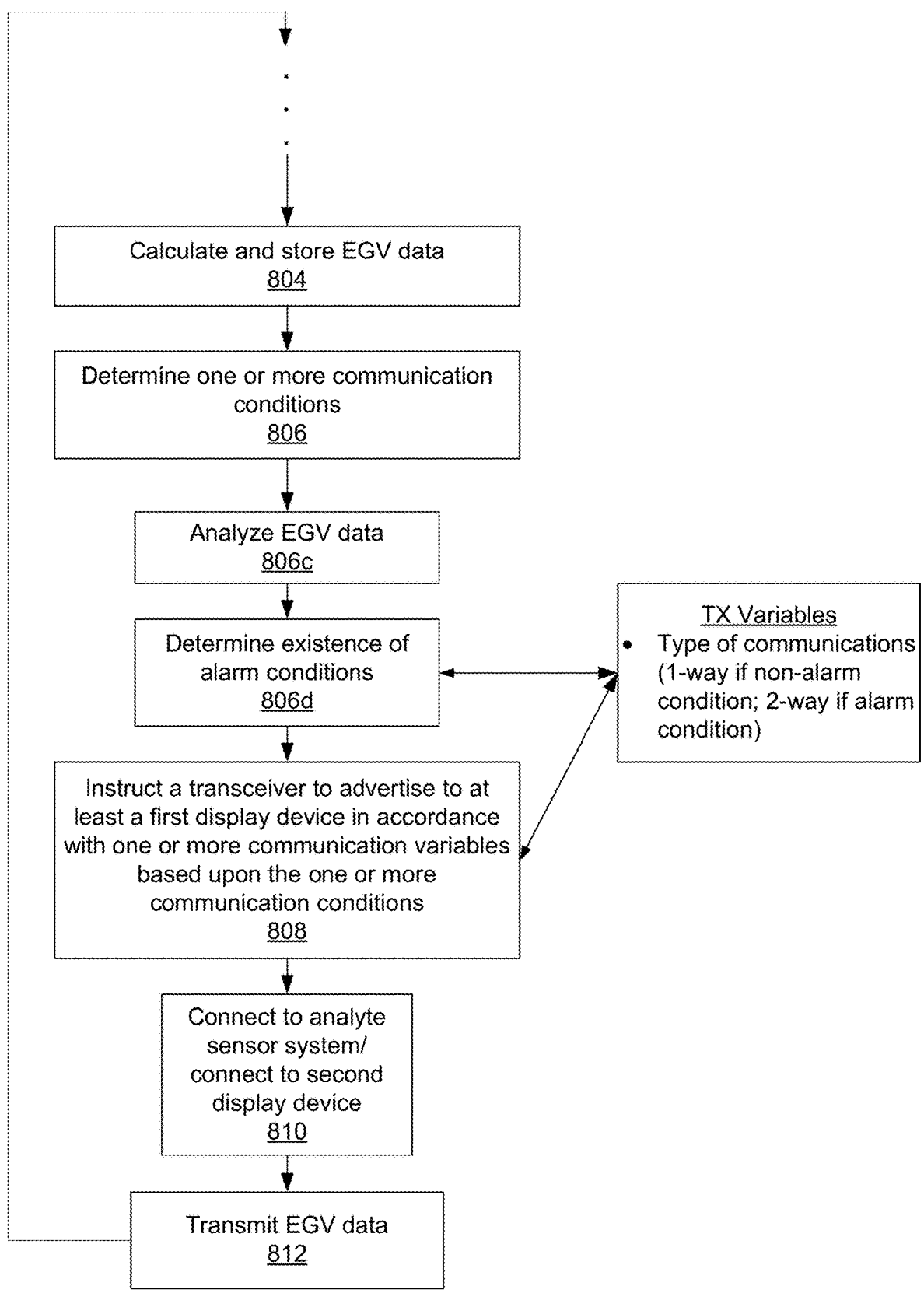

FIG. 8H is a flow chart illustrating example processes performed in accordance with the above example scenario, and will be described with reference to previously described FIGS. 1, 6, and 7 for ease of understanding. CGM processor 506 may calculate an EGV value and store that calculated EGV value (operation 804 and process 604 of FIG. 6). It should be understood that operations 800 and 802 (illustrated in FIG. 8A) may have already been performed. In accordance with one or more algorithms utilized in controlling CGM processor 506, CGM processor 506 may be instructed to determine one or more communication conditions (operation 806). In accordance with one example, CGM processor 506 may be instructed to analyze EGV data (operation 806*c*) which includes historical EGV data. Thus CGM processor 506 may access its database and review some predetermined number (or for some predetermined amount of time) calculated EGV values to determine a recent trend of analyte (in this case, glucose) measurements. If the observed trend of analyte measurements indicates that the user (e.g., host 102 of FIG. 1) may be falling into a hypoglycemic condition, CGM processor 506 can determine the existence of an alarm condition (operation 806*d*). Based on this determination that an alarm condition exists, the type of communications will be set to 2-way communications or a different wireless protocol may be implemented, and advertising can commence (operation 808). Accordingly, a display device, e.g., display device 120*c*, connects to analyte sensor system 104 and establishes a wireless communication session (operation 810). Moreover, the EGV data is transmitted at operation 812. If desired, the user can request EGV data on-demand (via, e.g., NFC-directed advertising), and operation returns to operation 800. However, if it is determined that an alarm condition does not exist, the type of communications will be set to 1-way communications, in which case, the advertising beacons can be configured to include EGV trend data, for example, and a wireless communications session need not be established (operation 808).

Further to the above, data packet formatting can be affected as well, e.g., one-way transmission of data can occur with unencrypted data, while two-way communication of data utilizes encrypted data, and vice-versa. Moreover, update alerts can be transmitted to one or more (secondary) display devices, such as display device 120*b* and/or display device 120*c*, instructing them to establish communications with a (primary) display device, such as display device 120*a*, to transmit a status update. Additionally still, previously stored/analyzed raw sensor data and/or EGV data can be used to predict possible user states, determine patterns associated with the user's states, e.g., throughout the day, learn the user's behavior that may impact his/her state, etc. Such data may then be utilized to determine what or when the next transmission of data should occur. Hence, the aforementioned mode of transmission and/or frequency of transmission can be adapted accordingly.

Additionally, the state of the analyte sensor system 104 can be a condition upon which communications may be altered. For example, as alluded to previously, a communication command may be used to ensure radio 508 does not exceed a predefined communication window. That is, and referring back to processes 612 of FIG. 6, a CGM transmit command comprises a response to a connection request for performing the reverse operations of the CGM receive command, i.e., it takes the payload and sends it to the radio stack to be transmitted on the RF link. A stop communication command may be used to ensure radio 508 does not exceed a predefined "communication window," which in some embodiments is, e.g., 30 seconds, since RF noise can affect AFE sensor measurements. This stop command accordingly can be sent, e.g., 26 seconds after the start communication command is sent. Moreover, the presence of excessive signal noise may suggest that communications with a particular display device should be stopped, and the transmission of data should continue with an alternative display device.

Direct transmission of analyte data can be implemented in an encrypted manner in/on an advertising beacon. That is, advertising beacons containing encrypted analyte data can be used to directly communicate those measured analyte values, e.g., glucose values, without establishing a two-way communication protocol. A display device can be allowed to select source information based on the establishment or lack of another connection. For example, in some embodiments, connection of a first display device can be determined, e.g., a wireless connection between analyte sensor system 104 and display device 120c. Data transmission of sensor information can be effectuated directly from display device 120c to a second display device, e.g., display device 120b. Otherwise, data transmission can occur between the analyte sensor system 104 and display device 120b. Additionally, an encryption scheme can be established using two-way communication pursuant to an initial transmission of data, e.g., a static display device encryption key can be used to avoid setting up two-way communication for each transmission.

The formatting of data packets may also include using one or more data compression techniques. In accordance with some embodiments, analog waveform compression techniques such as Fourier transformation, etc. can be used to compress the EGV data resulting in much smaller transmissions, which in turn results in reduced battery use. For example, and referring back to FIG. 4, first and second data connections 416 and 424 can be shortened in duration. In accordance with other embodiments, the transmission of data can be reduced by, e.g., not transmitting backfill data, calibration data, etc. unless needed. For example, if a user's state is not critical or an analyzed data trend suggests that the user's state is safely within a "cone of possibilities," backfill data need not be transmitted from analyte sensor system 104 to one or more of display devices 120. In still other embodiments, an initial data transmission (or an advertising beacon, e.g., advertising beacons 700 of FIG. 7) can include information indicating to one or more display devices, e.g., display device 120c, what type of data will be forthcoming in a subsequent transmission. In this way, a user can refuse or deny backfill data if it is not needed, or display device 120c may be able to determine on its own that such data need not be received.

A scenario in which this may arise is when the user may have forgotten one or more of his/her display devices 120, and thus, an extended period of time goes by in which analyte sensor system 104 does not connect to any of the display devices 120. Upon the user, e.g., returning to his/her home, and at least one of display devices 120 responding to an advertising beacon, e.g., display device 120c responding to advertising beacons 700 (also illustrated as authentication/channel establishment/data connection establishment 414 of FIG. 4), the user can decide whether or not to receive backfill sensor information. That is, if the user is sufficiently certain that he/she is not approaching or in potentially adverse condition, he/she can refuse the backfill sensor information. Alternatively, display device 120c may receive an initial EGV that suggests that the user is in a stable condition, in which case, display device 120c may determine (according to a predictive algorithm) that backfill sensor information is not needed.

In accordance with some embodiments, alternative or additional communication protocols/methods can be leveraged to reduce battery consumption, e.g., NFC. For example, a connected display device, e.g., display device 120b, may only receive communications from the analyte sensor system 104 that triggers a notification to be presented to the user or an indicator to light and/or emit sound instructing the user to swipe or touch display device 120b or another display device, e.g., 120c, to the analyte system sensor 104 in order to receive data transmission via NFC, rather than consuming battery power with conventional wireless communication of the data. Moreover, out-of-band NFC pairing of a display device, e.g., display device 120c, to the analyte sensor system 104 can be used, where a user need only tap display device 120c to the analyte sensor system 104 to connect to and initiate data transmission from analyte sensor system 104. This negates the need to wait for advertising beacons (described previously) and the need to send a command request (illustrated as 412 in FIG. 4, and 614 in FIG. 6, respectively). The whitelist as well, may be populated and/or updated in a similar manner to achieve "user-selective" pairing, where the exchange of keys and bonding information, as well as the passing of authentication/authorization information can also occur via NFC. It should be noted that sensor electronics module 106 (described above) can be configured to include an NFC transceiver in addition to the radio 508.

As with intelligent advertising, intelligent communication can also utilize alternative networking techniques, e.g., mesh, peer-to-peer, or cloud networking. Similar to allowing a display device, such as display device 120c, to advertise to additional display devices, such as display device 120b, display device 120c can also be utilized to connect to and transmit EGV data to display device 120b, thereby limiting the amount of connections to/transmissions from the analyte sensor system 104. The transmitting display device, in this case display device 120c, can be used to perform the necessary setup/handshaking between the additional display devices, in this case display device 120b, e.g., exchange of encryption keys, determining display device type, etc.

Figure 9:
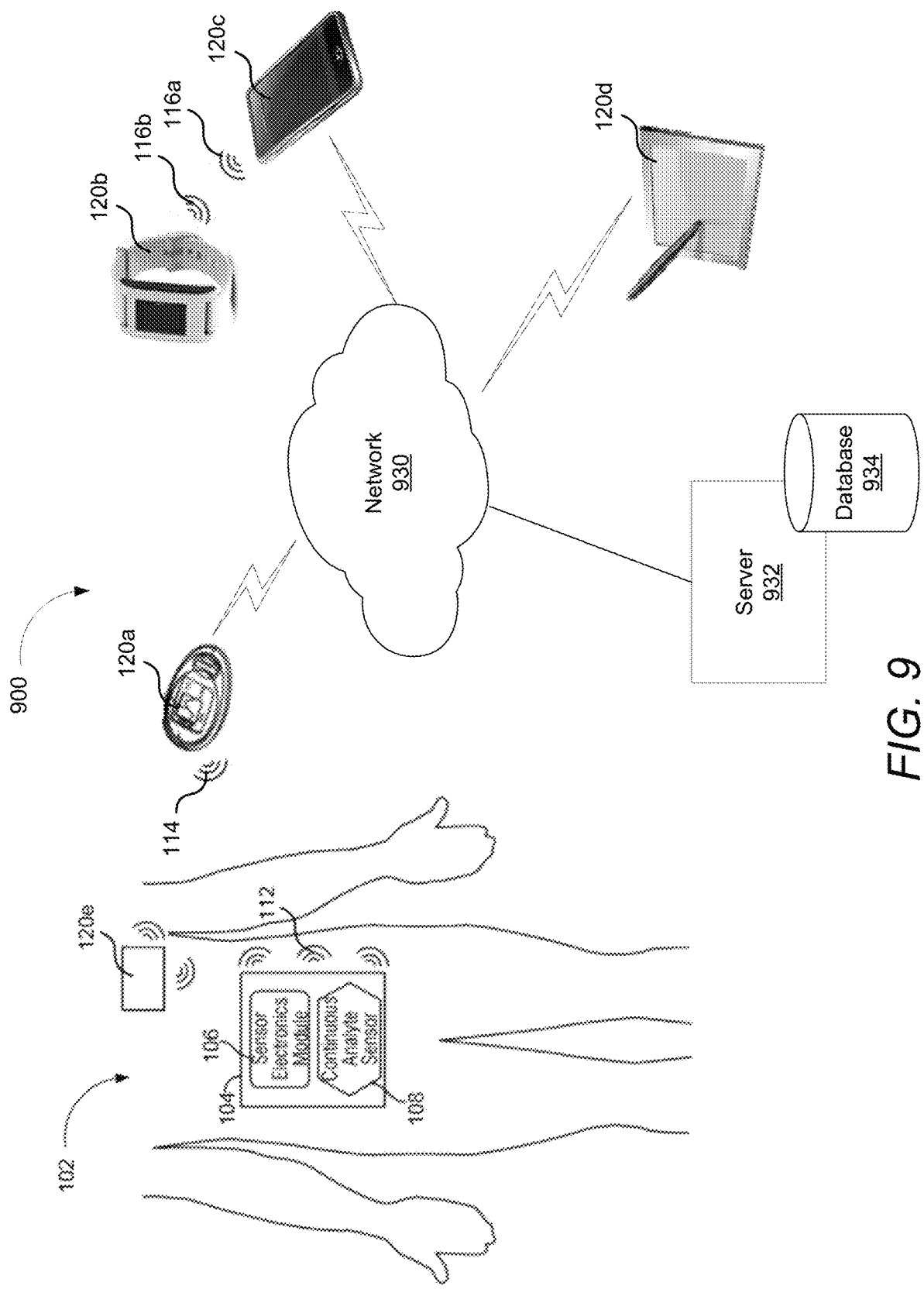
FIG. 9 is a diagram illustrating certain alternative examples of a continuous analyte sensor system communicating with at least one display device in accordance with various technologies described in the present disclosure.

FIG. 9 illustrates an example continuous analyte monitoring system 900 (which may be an embodiment of the continuous analyte monitoring system 100 of FIG. 1) and a plurality of alternative networking options contemplated in accordance with various embodiments. In accordance with one embodiment described above, display device 120c and be used to advertise (transmit advertising beacons) to additional display devices, in this example, display device 120*b*. Crosslink signals 116*a* and *b* can be used to effectuate the aforementioned encryption key exchange, setup/handshaking, display device type determination, etc.

In some embodiments, such alternative networking techniques may be used to backfill data on one or more display devices. For example, and referring again to FIG. 9, a primary display device, such as display device 120*a*, may have up-to-date and complete EGV data, where display device 120*a* can then be used to transmit backfill data to one or more secondary display devices if needed, rather than relying on the analyte sensor system 104 to transmit backfill data, again, reducing battery power consumption on the analyte sensor system 104. FIG. 9 illustrates that display device 120*a* may obtain EGV data and/or engage in wireless communications with analyte sensor system 104 using uplink signals 114 and downlink signals 112. In the case of cloud networking, secondary display devices, such as display device 120*d*, may receive requisite data that has been uploaded to the cloud network (network 930 which can include a remote server 932 and/or associated database 934) via the primary display device, display device 120*a* again reducing the strain on the analyte sensor system 104. In some embodiments, the entity providing analyte sensor system 104 may maintain server 932 and database 934. Further still, the analyte system sensor 104 and/or display device 120*a*, for example, can be made aware of secondary display devices that may require data, in which case, analyte sensor system 104 may then engage in selective data transmission rather than broadcast transmission. This may be the case with display device 120*e*, for example.

It should be noted that a plurality of methods and/or techniques may be used to effectuate the embodiments disclosed in the present disclosure. That is, the above-described communication conditions and adjustment of communication variables can be rules or instructions (e.g., in the form of a matrix or matrices) used by one or more algorithms that can control operation of the analyte sensor system 104, in particular, CGM processor 506 and/or the transceiver, e.g., radio 508, NFC transceiver, etc. Moreover, the analyte sensor system 104 can learn from itself and "create" such rules. It should also be noted that various combinations of the above-mentioned embodiments/operational scenarios can be combined in different ways to achieve one or more desired operational characteristics in a continuous analyte measurement system. Although various embodiments have been described in the context of continuous analyte measurement, e.g., continuous glucose monitoring, the various embodiments can be adapted for use in other context as well, e.g., for monitoring vital signals.

Figure 10:
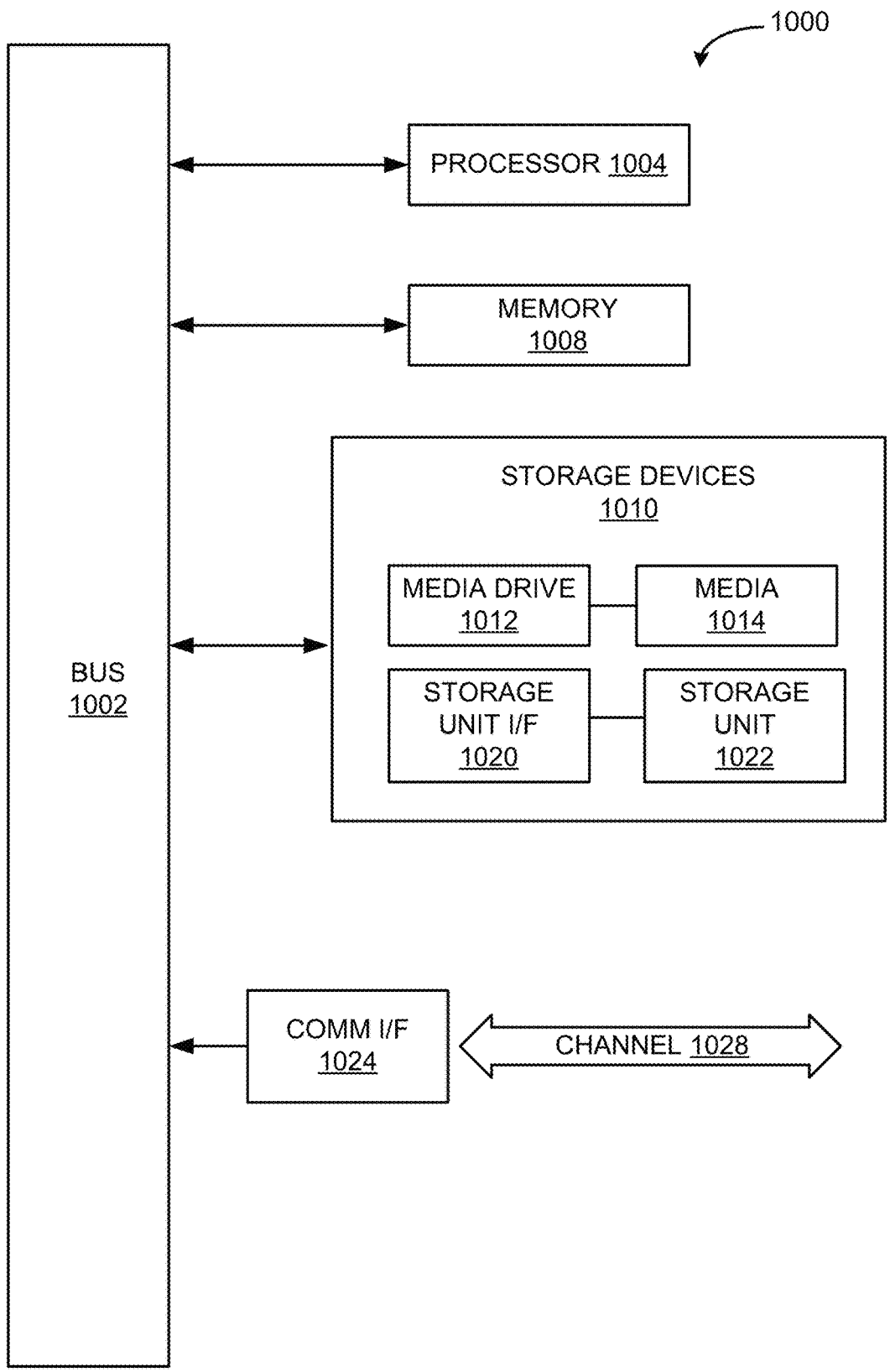
FIG. 10 is a block diagram of an example computing module that may be used to implement various features of embodiments described in the present disclosure.

As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. The modules, circuitry, processors, etc. may be affixed to a printed circuit board (PCB), or the like, and may take a variety of forms. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 10 which may be used to implement various features of the system and methods disclosed herein. Various embodiments are described in terms of this example computing module 1000. After reading this description, it will become apparent to a person skilled in the relevant art how to implement the application using other computing modules or architectures.

Referring now to FIG. 10, computing module 1000 may represent, for example, computing or processing capabilities found within a self-adjusting display, desktop, laptop, notebook, and tablet computers; hand-held computing devices (tablets, PDA's, smart phones, cell phones, palmtops, etc.); workstations or other devices with displays; servers; or any other type of special-purpose or general-purpose computing devices as may be desirable or appropriate for a given application or environment. For example, computing module 1000 may be one embodiment of one of display devices 120, sensor electronics module 106, etc. Computing module 1000 might also represent computing capabilities embedded within or otherwise available to a given device. For example, a computing module might be found in other electronic devices such as, for example, portable computing devices, and other electronic devices that might include some form of processing capability.

Computing module 1000 might include, for example, one or more processors, controllers, control modules, or other processing devices, such as a processor 1004. Processor 1004 might be implemented using a general-purpose or special-purpose processing engine such as, for example, a microprocessor, controller, or other control logic. In the illustrated example, processor 1004 is connected to a bus 1002, although any communication medium can be used to facilitate interaction with other components of computing module 1000 or to communicate externally.

Computing module 1000 might also include one or more memory modules, simply referred to herein as main memory 1008. For example, preferably random access memory (RAM) or other dynamic memory might be used for storing information and instructions to be executed by processor 1004. Main memory 1008 might also be used for storing temporary variables or other intermediate information during execution of instructions to be executed by processor 1004. Computing module 1000 might likewise include a read only memory ("ROM") or other static storage device coupled to bus 1002 for storing static information and instructions for processor 1004.

The computing module 1000 might also include one or more various forms of information storage mechanism 1010, which might include, for example, a media drive 1012 and a storage unit interface 1020. The media drive 1012 might include a drive or other mechanism to support fixed or removable storage media 1014. For example, a hard disk drive, a solid state drive, a magnetic tape drive, an optical disk drive, a compact disc (CD) or digital video disc (DVD) drive (R or RW), or other removable or fixed media drive might be provided. Accordingly, storage media 1014 might include, for example, a hard disk, an integrated circuit assembly, magnetic tape, cartridge, optical disk, a CD or DVD, or other fixed or removable medium that is read by, written to or accessed by media drive 1012. As these examples illustrate, the storage media 1014 can include a computer usable storage medium having stored therein computer software or data.

In alternative embodiments, information storage mechanism 1010 might include other similar instrumentalities for allowing computer programs or other instructions or data to be loaded into computing module 1000. Such instrumentalities might include, for example, a fixed or removable storage unit 1022 and an interface 1020. Examples of such storage units 1022 and interfaces 1020 can include a program cartridge and cartridge interface, a removable memory (for example, a flash memory or other removable memory module) and memory slot, a PCMCIA slot and card, and other fixed or removable storage units 1022 and interfaces 1020 that allow software and data to be transferred from the storage unit 1022 to computing module 1000.

Computing module 1000 might also include a communications interface 1024. Communications interface 1024 might be used to allow software and data to be transferred between computing module 1000 and external devices. Examples of communications interface 1024 might include a modem or softmodem, a network interface (such as an Ethernet, network interface card, WiMedia, IEEE 802.XX or other interface), a communications port (such as for example, a USB port, IR port, RS232 port Bluetooth® interface, Bluetooth Low Energy, or other port), or other communications interface. Software and data transferred via communications interface 1024 might typically be carried on signals, which can be electronic, electromagnetic (which includes optical) or other signals capable of being exchanged by a given communications interface 1024. These signals might be provided to communications interface 1024 via a channel 1028. This channel 1028 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 1008, storage unit 1020, media 1014, and channel 1028. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 1000 to perform features or functions of the present application as discussed herein.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the present disclosure, but instead as merely intended to highlight alternative or additional features that may or may not be utilized in a particular embodiment. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the present disclosure to the specific embodiments and examples described herein, but rather to also cover all modification and alternatives coming with the true scope and spirit of the present disclosure.

Exemplary Methods and Apparatus

Method 1. A computer-implemented method, comprising: receiving sensor information; calculating and storing estimated analyte measurement values based upon the received sensor information; determining one or more communication conditions; instructing a transceiver to advertise to at least a first display device in accordance with one or more communication variables based upon the one or more communication conditions; and transmitting the estimated analyte measurement values to the at least first display device.

Method 2. The computer-implemented method of Method 1, wherein the sensor information is received from a continuous glucose monitoring sensor.

Method 3. The computer-implemented method of Method 1 or 2, wherein the analyte measurement values comprise estimated glucose values.

Method 4. The computer-implemented method of Method 1 or 2, wherein determining the one or more communication conditions comprises determining at least one of the following: a time associated with the communication conditions; historical communication conditions; an existence of an alarm condition; a condition of the continuous glucose monitoring sensor; a condition of a user of the continuous glucose monitoring sensor; and whitelist conditions.

Method 5. The computer-implemented method of Method 4, wherein the first display device is determined to be proximate to the continuous glucose monitoring sensor based upon the time at which the estimated analyte measurement values are to be transmitted.

Method 6. The computer-implemented method of Method 5, wherein the one or more communication variables comprise at least one of an advertising duration parameter and an advertising interval parameter according to which advertising beacons are transmitted to the first display device, and wherein the at least one of the advertising duration and advertising interval parameters are adjusted to the first display device.

Method 7. The computer-implemented method of Method 4, wherein the first display device comprises one of a last-connected display device populating the whitelist, a preferred display device populating the whitelist, and a display device configured to advertise to at least a second display device.

Method 8. The computer-implemented method of Method 4, wherein the alarm condition comprises a determination that the condition of the user is approaching or experiencing a medically critical state.

Method 9. The computer-implemented method of Method 8, wherein the one or more communication variables are optimized for establishing a wireless communication session with the first display device.

Method 10. The computer-implemented method of Method 9, wherein the optimization of the one or more communication variables comprise at least one of increasing a default advertising duration parameter and decreasing a default advertising interval parameter.

Method 11. The computer-implemented method of Method 1 or 2, wherein determining the one or more communication conditions comprises analyzing the estimated analyte measurement values.

Method 12. The computer-implemented method of Method 11, wherein the one or more communication variables are optimized for establishing a wireless communication session with the first display device upon a determination that the estimated analyte measurement values are indicative of a trend towards a medically critical state.

Method 13. The computer-implemented method of Method 11, wherein the one or more communication variables are adjusted for delaying establishment of a wireless communication session with the first display device upon a determination that the estimated analyte measurement values are indicative of a trend towards a medically non-critical state.

Apparatus 14. An apparatus, comprising: signal conditioning circuitry communicatively connected to a continuous analyte sensor for receiving sensor information from the continuous analyte sensor indicative of analyte levels of a host to which the continuous analyte sensor is operatively attached; a processor, wherein upon receiving the sensor information from the signal conditioning circuitry, instructs a radio to perform the following: transmit a plurality of advertising beacons to a first display device in accordance with one or more communication variables based upon one or more communication conditions determined by the apparatus; and upon the first display device responding to one of the plurality of advertising beacons, establish a wireless communication session with the first display device and transmit the sensor information or analyte values derived from the sensor information to the at least first display device.

Apparatus 15. The apparatus of Apparatus 14, wherein the sensor information comprises raw sensor data indicative of glucose levels of the host, and wherein the analyte values derived from the sensor information comprises estimated glucose values of the host.

Apparatus 16. The apparatus of Apparatus 14 or 15, wherein the one or more communication variables comprise at least one of: a transmission frequency variable indicating a frequency with which the sensor information or the analyte values are transmitted to the first display device; a transmission protocol indicating a wireless communication protocol to be utilized in the transmission of the sensor information or the analyte values to the first display device; a communications type variable indicating a one-way communication or a two-way communication with the first display during the transmission of the sensor information or the analyte values to the first display device; and a transmission occurrence variable indicating whether the transmission of the sensor information or the analyte values to the first display device are to occur in an on-demand or automatic manner.

Apparatus 17. The apparatus of Apparatus 14 or 15, wherein the one or more communication variables comprise at least one of: a data packet format type variable to be utilized for the transmission of the plurality of advertising beacons; an advertising duration variable indicative of a duration for which the first display device is to be advertised to; an advertising interval variable indicative of an amount of time between the transmission of each of the plurality of advertising beacons; and a power variable indicative of power to be used by the radio for the transmission of the advertising beacons.

Apparatus 18. The apparatus of Apparatus 14 or 15, wherein the one or more communication variables comprise at least one of: a display device type variable indicating a type of at least one of the first display device and additional display devices to which the sensor information or analyte values are to be sent; a display device number indicating a number of display devices available to receive the sensor information or analyte values; an order variable indicating a connection order of display devices previously having established a wireless communication session with the radio; a role variable indicating whether at least one of the first display device and the additional display devices are at least one of a primary display device, a secondary display device, a preferred display device, a scan-only display device, an advertising display device, and a sensor information or analyte values forwarding display device; and a broadcast mode variable indicating one-way or two-way broadcasting to be used in conjunction with at least one of the first display device and the additional display devices if the at least one of the first display device and the additional display devices comprise an advertising display device or a sensor information or analyte values forwarding display device.

Method 19. A computer-implemented method, comprising: calculating and storing estimated glucose value data based upon glucose measurements obtained by a continuous glucose monitoring sensor; determining one or more communication conditions; and advertising to one or more display devices in a manner based on the one or more communication conditions.

Method 20. The computer-implemented method of Method 19, wherein the determination of the one or more communication conditions comprises analyzing historical estimated glucose value data.

Method 21. The computer-implemented method of Method 19 or 20, wherein the analysis of the historical estimated glucose value data results in an observed trend.

Method 22. The computer-implemented method of Method 21, wherein the determination of the one or more communication conditions further comprises determining whether an alarm condition exists based on the observed trend.

Method 23. The computer-implemented method of Method 22, wherein the advertising to the one or more displays comprises incorporating the estimated glucose value data in advertising beacons upon a determination that no alarm condition exists.

Method 24. The computer-implemented method of Method 23, wherein the estimated glucose value data is incorporated in the advertising beacons in an encrypted format.

Method 25. The computer-implemented method of Method 24, wherein the advertising to the one or more displays comprises transmitting advertising beacons to the one or more display devices upon a determination that an alarm condition exists.

Method 26. The computer-implemented method of Method 25, wherein the advertising beacons are transmitted in accordance with at least one of an advertising duration and an advertising interval optimized for the one or more display devices.

Method 27. The computer-implemented method of Method 26, further comprising establishing wireless communication sessions during which the estimated glucose value data is transmitted to the one or more display devices upon the one or more display devices responding to their respective advertising beacons.

Method 28. The computer-implemented method of Method 27, further comprising encrypting the estimated glucose value prior to transmission to the one or more display devices.

Apparatus 29. An apparatus, comprising: a continuous analyte sensor adapted to obtain raw analyte data; a processor and a memory unit having computer code configured to cause the processor to: calculate and store analyte value data derived from the raw analyte data; determine one or more communication conditions; and a radio adapted to advertise to one or more display devices in a manner based on the one or more communication conditions.

Apparatus 30. The apparatus of Apparatus 29, wherein the computer code configured to cause the processor to determine the one or more communication conditions comprises computer code configured to further cause the processor to analyze historical analyte value data.

Apparatus 31. The apparatus of Apparatus 29 or 30, wherein the computer code configured to further cause the processor to analyze the historical analyte value data comprises computer code configured to further cause the processor to determine a trend.

Apparatus 32. The apparatus of Apparatus 31, wherein the computer code configured to cause the processor to determine the one or more communication conditions comprises computer code configured to further cause the processor to determine whether an alarm condition exists based on the trend.

Apparatus 33. The apparatus of Apparatus 32, wherein the computer code configured to cause the processor to advertise to the one or more displays comprises computer code configured to further cause the processor to incorporate the analyte value data in advertising beacons upon a determination that no alarm condition exists.

Apparatus 34. The apparatus of Apparatus 33, wherein the analyte value data is incorporated in the advertising beacons in an encrypted format.

Apparatus 35. The apparatus of Apparatus 34, wherein the computer code configured to cause the processor to advertise to the one or more displays comprises computer code configured to cause the processor to transmit advertising beacons to the one or more display devices upon a determination that an alarm condition exists.

Apparatus 36. The apparatus of Apparatus 35, wherein the computer code configured to further cause the processor to transmit advertising beacons comprises computer code configured to cause the processor to transmit the advertising beacons in accordance with at least one of an advertising duration and an advertising interval optimized for the one or more display devices.

Apparatus 37. The apparatus of Apparatus 36, wherein the radio establishes wireless communication sessions with of the one or more display devices during which the analyte value data is transmitted to the one or more display devices upon the one or more display devices responding to their respective advertising beacons.

Apparatus 38. The apparatus of Apparatus 37, wherein the computer code is configured to further cause the processor to encrypt the analyte value data prior to transmission to the one or more display devices.

Apparatus 39. An apparatus, comprising: a memory; and a processor, the memory having computer code configured to cause the processor to: receive estimated glucose value data; and based upon observed communication conditions and communication variables adapted based on the observed communication conditions, transmit the estimated glucose value data to one or more display devices.

Apparatus 40. The apparatus of Apparatus 39, wherein the apparatus comprises a primary or preferred display device, and wherein the estimated glucose value data is received from a sensor electronics module of a continuous glucose monitoring sensor system.

Apparatus 41. The apparatus of Apparatus 40, wherein the estimated glucose value data is transmitted to a remote database for storage via a network and forwarded to the one or more display devices by a server operatively connected to the database via the network, wherein the one or more display devices comprise secondary display devices.

Apparatus 42. The apparatus of Apparatus 40 or 41, wherein the apparatus and the one or more display devices are denoted as being the primary or preferred display device and secondary display devices, respectively, within a whitelist maintained by the continuous glucose monitoring sensor system.

Apparatus 43. The apparatus of Apparatus 39, wherein the apparatus comprises a first display device configured to act as an advertising display device, and wherein the apparatus transmits advertising beacons to the one or more display devices on behalf of a continuous glucose monitoring sensor system.

Apparatus 44. The apparatus of Apparatus 39, wherein the apparatus comprises a first display device configured to act as a forward display device, and wherein the apparatus transmits the estimated glucose value data to the one or more display devices on behalf of a continuous glucose monitoring sensor system.

Apparatus 45. The apparatus of Apparatus 39, further comprising a near field communications module adapted to cause a sensor electronics module of a continuous glucose monitoring sensor system from which the estimated glucose value data is received, to initiate advertising processes for establishing a wireless communication session over which the estimated glucose value data is transmitted with at least one of the apparatus and the one or more display devices.

Any of the features of the exemplary methods and apparatus are applicable to all aspects and embodiments identified herein, including other exemplary methods and apparatus. Moreover, any of the features of the exemplary methods and apparatus are independently combinable, partly or wholly with other aspects and embodiments identified herein or other exemplary methods and apparatus described herein in any way, e.g., one, two, or three or more aspects, embodiments, exemplary methods and/or apparatus may be combinable in whole or in part. Further, any of the features of the exemplary methods and apparatus may be made optional to other aspects or embodiments. Any aspect or embodiment of a method may be performed by a system or apparatus of another aspect or embodiment, and any aspect or embodiment of a system or apparatus may be configured to perform a method of another aspect or embodiment.

What is claimed is:

1. A computer-implemented method, comprising:
receiving sensor information;
calculating and storing estimated analyte measurement values based upon the received sensor information;
determining one or more communication conditions including an existence of an alarm condition;
instructing a transceiver to advertise to at least a first display device according to a type of communication, the transceiver switching between one-way communication and two-way communication according to the existence of the alarm condition; and
transmitting the estimated analyte measurement values to the at least first display device.

2. The computer-implemented method of claim 1, wherein the sensor information is received from a continuous glucose monitoring sensor.

3. The computer-implemented method of claim 2, wherein determining the one or more communication conditions further comprises determining at least one of the following:
   a time associated with the one or more communication conditions;
   historical communication conditions;
   a condition of the continuous glucose monitoring sensor;
   a condition of a user of the continuous glucose monitoring sensor; or
   whitelist conditions.

4. The computer-implemented method of claim 3, wherein the at least first display device is determined to be proximate to the continuous glucose monitoring sensor based upon a time at which the estimated analyte measurement values are to be transmitted.

5. The computer-implemented method of claim 4, wherein the transceiver advertises to the at least first display device in accordance with one or more communication variables including at least one of an advertising duration parameter or an advertising interval parameter according to which advertising beacons are transmitted to the at least first display device, and wherein the at least one of the advertising duration or advertising interval parameters is adjusted to the at least first display device.

6. The computer-implemented method of claim 3, wherein the at least first display device comprises one of a last-connected display device populating a whitelist, a preferred display device populating the whitelist, or a display device configured to advertise to at least a second display device.

7. The computer-implemented method of claim 1, wherein the estimated analyte measurement values comprise estimated glucose values.

8. The computer-implemented method of claim 1, wherein the alarm condition comprise s a determination that a condition of a user is approaching or experiencing a medically critical state.

9. The computer-implemented method of claim 8, wherein the transceiver advertises to the at least first display device in accordance with one or more communication variables optimized for establishing a wireless communication session with the at least first display device.

10. The computer-implemented method of claim 9, wherein the optimization of the one or more communication variables comprise at least one of increasing a default advertising duration parameter or decreasing a default advertising interval parameter.

11. The computer-implemented method of claim 1, wherein determining the one or more communication conditions comprises analyzing the estimated analyte measurement values.

12. The computer-implemented method of claim 11, wherein the transceiver advertises to the at least first display device in accordance with one or more communication variables optimized for establishing a wireless communication session with the at least first display device upon a determination that the estimated analyte measurement values are indicative of a trend towards a medically critical state.

13. The computer-implemented method of claim 11, wherein the transceiver advertises to the at least first display device in accordance with one or more communication variables that are adjusted for delaying establishment of a wireless communication session with the at least first display device upon a determination that the estimated analyte measurement values are indicative of a trend towards a medically non-critical state.

14. An apparatus, comprising:
   signal conditioning circuitry communicatively connected to a continuous analyte sensor for receiving sensor information from the continuous analyte sensor indicative of analyte levels of a host to which the continuous analyte sensor is operatively attached;
   a processor, upon receiving the sensor information from the signal conditioning circuitry, configured to instruct a radio to perform the following:
      transmit one or more advertising beacons to a first display device according to a type of communication, the radio switching between one-way communication and two-way communication according to an existence of an alarm condition determined by the apparatus; and
      upon the first display device responding to one of the one or more advertising beacons, establish a wireless communication session with the first display device and transmit the sensor information or analyte values derived from the sensor information to the first display device.

15. The apparatus of claim 14, wherein the sensor information comprises raw sensor data indicative of glucose levels of the host, and wherein the analyte values derived from the sensor information comprise estimated glucose values of the host.

16. The apparatus of claim 15, wherein the radio transmits the one or more advertising beacons in accordance with one or more communication variables comprising at least one of:
   a transmission frequency variable indicating a frequency with which the sensor information or the analyte values are transmitted to the first display device;
   a transmission protocol indicating a wireless communication protocol to be utilized in the transmission of the sensor information or the analyte values to the first display device; or
   a transmission occurrence variable indicating whether the transmission of the sensor information or the analyte values to the first display device are to occur in an on-demand or automatic manner.

17. The apparatus of claim 15, wherein the radio transmits the one or more advertising beacons in accordance with one or more communication variables comprising at least one of:
   a data packet format type variable to be utilized for the transmission of the one or more advertising beacons;
   an advertising duration variable indicative of a duration for which the first display device is to be advertised to;
   an advertising interval variable indicative of an amount of time between the transmission of each advertising beacon, wherein the one or more advertising beacons are a plurality of advertising beacons; or
   a power variable indicative of power to be used by the radio for the transmission of the one or more advertising beacons.

18. The apparatus of claim 15, wherein the radio transmits the one or more advertising beacons in accordance with one or more communication variables comprising at least one of:
   a display device type variable indicating a type of at least one of the first display device or additional display devices to which the sensor information or analyte values are to be sent;
   a display device number indicating a number of display devices available to receive the sensor information or analyte values;

an order variable indicating a connection order of display devices previously having established a wireless communication session with the radio; or a role variable indicating whether at least one of the first display device or the additional display devices is at least one of a primary display device, a secondary display device, a preferred display device, a scan-only display device, an advertising display device, or a sensor information or analyte values forwarding display device.

19. A computer-implemented method, comprising:

calculating and storing estimated glucose value data based upon glucose measurements obtained by a continuous glucose monitoring sensor;

determining one or more communication conditions including an existence of an alarm condition; and advertising, by a transceiver, to one or more display devices according to a type of communication the transceiver switching between one-way communication and two-way communication according to the existence of the alarm condition.

20. The computer-implemented method of claim 19, wherein the determination of the one or more communication conditions further comprises analyzing historical estimated glucose value data.

21. The computer-implemented method of claim 20, wherein the analysis of the historical estimated glucose value data results in an observed trend.

22. The computer-implemented method of claim 21, wherein the determination of the one or more communication conditions comprises determining whether the alarm condition exists based on the observed trend.

23. The computer-implemented method of claim 22, wherein the advertising to the one or more display devices comprises incorporating the estimated glucose value data in advertising beacons upon a determination that no alarm condition exists.

24. The computer-implemented method of claim 23, wherein the estimated glucose value data is incorporated in the advertising beacons in an encrypted format.

25. The computer-implemented method of claim 24, wherein the advertising to the one or more display devices comprises transmitting advertising beacons to the one or more display devices upon a determination that the alarm condition exists.

26. The computer-implemented method of claim 25, wherein the advertising beacons are transmitted in accordance with at least one of an advertising duration or an advertising interval optimized for the one or more display devices.

27. The computer-implemented method of claim 26, further comprising establishing wireless communication sessions during which the estimated glucose value data is transmitted to the one or more display devices upon the one or more display devices responding to their respective advertising beacons.

28. The computer-implemented method of claim 27, further comprising encrypting the estimated glucose value data prior to transmission to the one or more display devices.

* * * * *